(12) United States Patent
Morishita et al.

(10) Patent No.: US 8,748,015 B2
(45) Date of Patent: *Jun. 10, 2014

(54) INDENOFLUORENEDIONE DERIVATIVE, MATERIAL FOR ORGANIC ELECTROLUMINESCENT ELEMENT, AND ORGANIC ELECTROLUMINESCENT ELEMENT

(71) Applicant: Idemitsu Kosan Co., Ltd., Chiyoda-ku (JP)

(72) Inventors: Hironobu Morishita, Sodegaura (JP); Yuichiro Kawamura, Sodegaura (JP); Jun Endo, Sodegaura (JP)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/017,058

(22) Filed: Sep. 3, 2013

(65) Prior Publication Data

US 2014/0001461 A1 Jan. 2, 2014

Related U.S. Application Data

(63) Continuation of application No. 13/132,141, filed as application No. PCT/JP2009/070243 on Dec. 2, 2009.

(30) Foreign Application Priority Data

Dec. 3, 2008 (JP) .................................. 2008-308963

(51) Int. Cl.
*H01L 51/00* (2006.01)
*C07C 255/35* (2006.01)
*C07C 255/37* (2006.01)
*C07C 261/04* (2006.01)

(52) U.S. Cl.
USPC ........... 428/690; 428/917; 313/504; 313/506; 564/105; 558/427; 257/40

(58) Field of Classification Search
None
See application file for complete search history.

(56) References Cited

U.S. PATENT DOCUMENTS 6,479,172 B2 * 11/2002 Hu et al. ..................... 428/690
6,562,485 B2 * 5/2003 Hu et al. ..................... 428/690

(Continued)

FOREIGN PATENT DOCUMENTS

| JP | 2002 329582 | 11/2002 |
|---|---|---|
| WO | 2009 011327 | 1/2009 |
| WO | 2009 069717 | 6/2009 |

OTHER PUBLICATIONS

Bethell et al., J. Chem. Soc. Perkin Trans. II, 1989, pp. 1105-1109.*

(Continued)

*Primary Examiner* — Dawn Garrett
(74) *Attorney, Agent, or Firm* — Oblon, Spivak, McClelland, Maier & Neustadt, L.L.P.

(57) ABSTRACT

An indenofluorenedione derivative having a specific structure, which is useful as a material for organic electroluminescence devices because the derivative is excellent in heat resistance and can be vapor-deposited on a substrate at moderate temperature. An organic electroluminescence device including an anode, a cathode, and an organic thin layer between the anode and the cathode, which contains the material for organic electroluminescence devices in the organic thin layer, is driven at a low driving voltage and has a long lifetime.

27 Claims, 1 Drawing Sheet

(56) References Cited

U.S. PATENT DOCUMENTS

| | | | |
|---|---|---|---|
| 2002/0132134 A1* | 9/2002 | Hu et al. | 428/690 |
| 2003/0008174 A1 | 1/2003 | Suzuki et al. | |
| 2003/0044646 A1* | 3/2003 | Hu et al. | 428/690 |
| 2009/0036643 A1 | 2/2009 | Marks et al. | |
| 2009/0315022 A1 | 12/2009 | Morishita et al. | |
| 2010/0044686 A1 | 2/2010 | Morishita | |
| 2011/0284827 A1* | 11/2011 | Morishita et al. | 257/40 |
| 2012/0012820 A1* | 1/2012 | Endo et al. | 257/40 |

OTHER PUBLICATIONS

Bethell et al., J. Chem. Soc. Perkin Trans. II, 1989, pp. 1097-1104.*

Helvetica Chimica Acta, (1951), vol. 34, pp. 168-185.*

Extended European Search Report issued Jun. 6, 2012, in European Patent Application No. 09830421.5.

Hakan Usta, et al., "Design, Synthesis, and Characterization of Ladder-Type Molecules and Polymers. Air-Stable, Solution-Processable n-Channel and Ambipolar Semiconductors for Thin-Film Transistors via Experiment and Theory", Journal of the American Chemical Society, vol. 131, No. 15, XP-55027940, Apr. 22, 2009, pp. 5586-5608.

Usta, H., et al., "Synthesis and Characterization of Electron-Deficient and Highly Soluble (Bis)Indenofluorene Building Blocks for n-Type Semiconducting Polymers", Organic Letters, vol. 10, No. 7, pp. 1385-1388, (Mar. 4, 2008).

Usta, H. et al., "Air-Stable Solution-Processable n-Channel and Ambipolar Semiconductors for Thin-Film Transistors Based on the Indenofluorenebis(Dicyanovinylene) Core", Journal of American Chemical Society, vol. 130, No. 27, pp. 8580-8581, (Jun. 11, 2008).

Internatioanl Search Report Issued Dec. 28, 2009 in PCT/JP09/070243 filed Dec. 2, 2009.

* cited by examiner

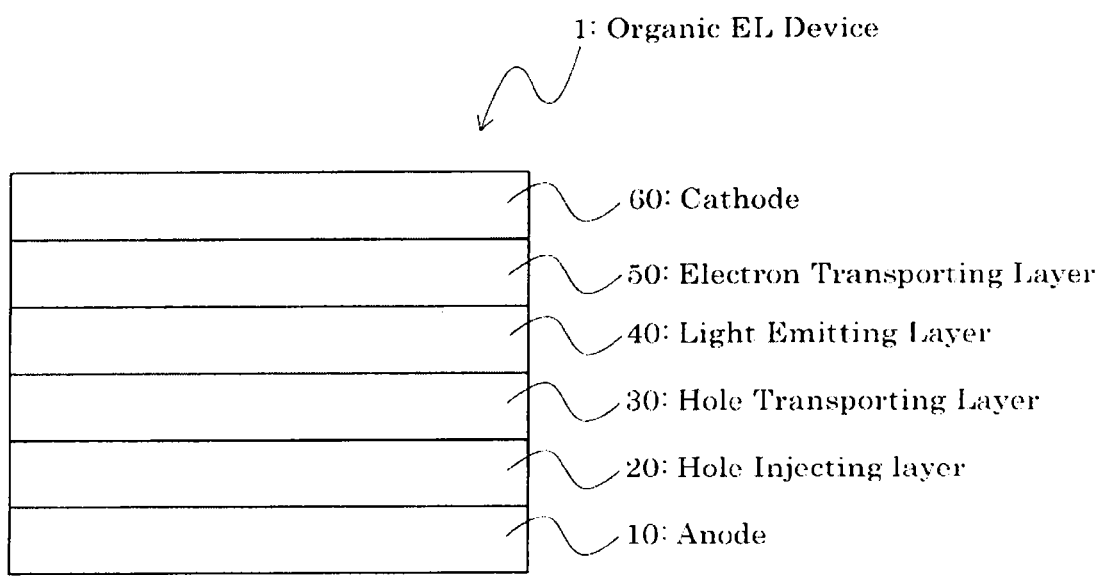

INDENOFLUORENEDIONE DERIVATIVE, MATERIAL FOR ORGANIC ELECTROLUMINESCENT ELEMENT, AND ORGANIC ELECTROLUMINESCENT ELEMENT

The present application is a continuation application of Ser. No. 13/132,141 having a filing date of Aug. 3, 2011 which is a national stage application of PCT/JP09/070243 having a filing date of Dec. 2, 2009, and claiming priority to Japanese Patent Application No. 2008-308963 having a filing date of Dec. 3, 2008.

TECHNICAL FIELD BACKGROUND ART

The present invention relates to a novel indenofluorenedione derivative, a material for organic electroluminescence device, and an organic electroluminescence device employing the material.

BACKGROUND ART

The organic electroluminescence device ("electroluminescence" may be referred to as "EL") is a spontaneous luminescence device in which a fluorescent material emits light by the energy of recombination of holes injected from an anode and electrons injected from cathode each being injected by the action of electric field.

A two-layered structure having a hole transporting (injecting) layer and an electron transporting, light emitting layer and a three-layered structure having a hole transporting (injecting) layer, a light emitting layer, and an electron transporting (injecting) layer are well known as the laminated structure of organic EL devices. To improve the efficiency of recombination of injected holes and electrons of organic EL devices of laminated structure type, the structure of device and the production method thereof have been studied.

An aromatic diamine derivative and a diamine derivative having an aromatic condensed ring have been used as the hole transporting material for known organic EL devices.

However, the organic EL device containing such aromatic diamine derivative as the hole transporting material involves the problems of reducing the lifetime of device and increasing the electric power to be consumed, because a high voltage is required to obtain sufficient luminance.

To solve the above problems, it has been proposed to dope an electron accepting compound such as Lewis acid to the hole injecting layer or use the electron accepting compound alone (for example, Patent Documents 1 to 4). However, the electron accepting compounds proposed in Patent Documents 1 to 4 involve the problems, because they are instable and difficult to handle in the production of organic EL devices, and the stability such as heat resistance is insufficient during the driving of organic EL devices, to reduce the lifetime.

Tetrafluorotetracyanoquinodimethane ($TCNQF_4$) exemplified in Patent Documents 3, 4, etc. is highly sublimable because of its low molecular weight and the fluorine substitution. Therefore, this compound diffuses throughout the apparatus during the production of organic EL device by a vacuum vapor deposition, thereby likely contaminating the apparatus and devices being produced (for example, Patent Document 5).

Patent Document 1: JP 2003-031365A
Patent Document 2: JP2001-297883A
Patent Document 3: JP2004-514257A
Patent Document 4: US 2005/0255334A1
Patent Document 5: JP2008-244430A

DISCLOSURE OF THE INVENTION

The present invention has been made to solve the above problems and an object of the present invention is to provide an indenofluorenedione derivative which is excellent in the heat resistance and can be vapor-deposited on a substrate at moderate temperature and a material for organic electroluminescence devices containing the indenofluorenedione derivative. A further object is to provide an organic electroluminescence device which is driven at a low driving voltage and has a long lifetime.

As a result of extensive research on the skeletons of various compounds, the inventors have paid attention to the skeleton of indenofluorenedione. The indenofluorenedione has in one molecule two quinone moieties (for example, $=X^1$ and $=X^2$ in formula (I) described below are both $=O$). By converting two quinone moieties to dicyanomethylene group, cyanoimino group, etc., the electron accepting property is enhanced as compared with a fluorenone derivative. The sublimation temperature of the fluorenone derivative is low because it has a small molecular weight and only one quinone moiety. This may result in the contamination of apparatus during the vapor deposition for film forming. In contrast, the indenofluorenedione derivative has good heat resistance and moderate deposition temperature because it has 5 or more aromatic rings or heterorings each being fused to each other, enabling a successful production of organic EL device by vapor deposition. In addition, the crystallization can be reduced by the conversion of two quinone moieties to dicyanomethylene group or cyanoimino group.

Further, the electron accepting property can be further enhanced and the crystallinity can be further reduced by introducing a specific substituent to the terminal rings.

The inventors have found that organic EL devices having a low driving voltage and a long lifetime are realized by producing the devices using the indenofluorenedione derivative having such properties as the material for organic EL devices, particularly by forming a hole injecting layer using the indenofluorenedione derivative.

Namely, the present invention relates to (1) an indenofluorenedione derivative represented by formula (I):

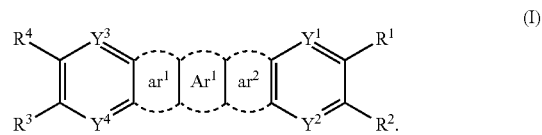

In formula (I), $Ar^1$ is a condensed ring having 6 to 24 nuclear carbon atoms or a heteroring having 6 to 24 nuclear atoms, and $ar^1$ and $ar^2$ may be the same or different and each independently represent a structure represented by formula (i) or (ii):

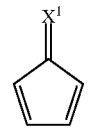

-continued

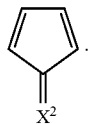
(ii)

In formulae (i) and (ii), $X^1$ and $X^2$ may be the same or different and selected from the following divalent groups represented by formulae (a) to (g):

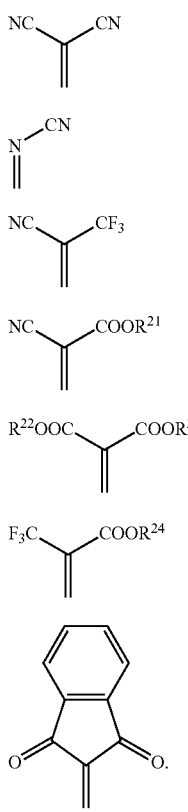

In formulae (d) to (f), $R^{21}$ to $R^{24}$ may be the same or different and each represent a hydrogen atom, a substituted or unsubstituted fluoroalkyl group, a substituted or unsubstituted alkyl group, a substituted or unsubstituted cycloalkyl group, a substituted or unsubstituted aryl group, or a substituted or unsubstituted heterocyclic group, and $R^{22}$ and $R^{23}$ may bond to each other to form a ring.

In formula (I), $R^1$ to $R^4$ may be the same or different and independently represent a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxyl group, a substituted or unsubstituted fluoroalkoxyl group, a substituted or unsubstituted aryloxy group, a substituted or unsubstituted aralkyloxy group, a substituted or unsubstituted amino group, or cyano group. $R^1$ and $R^2$, and $R^3$ and $R^4$ may bond to each other to form a saturated or unsaturated divalent group completing a ring. $Y^1$ and $Y^1$ may be the same or different and represent $-N=$, $-CH=$, or $-C(R^5)=$, wherein $R^5$ is defined in the same manner as in $R^1$ to $R^4$. Adjacent groups of $R^1$ to $R^5$ may bond to each other to form a saturated or unsaturated divalent group completing a ring.

However, the indenofluorenedione derivative represented by formula (I) does not include the compound represented by formula (iii), (iv), or (v).

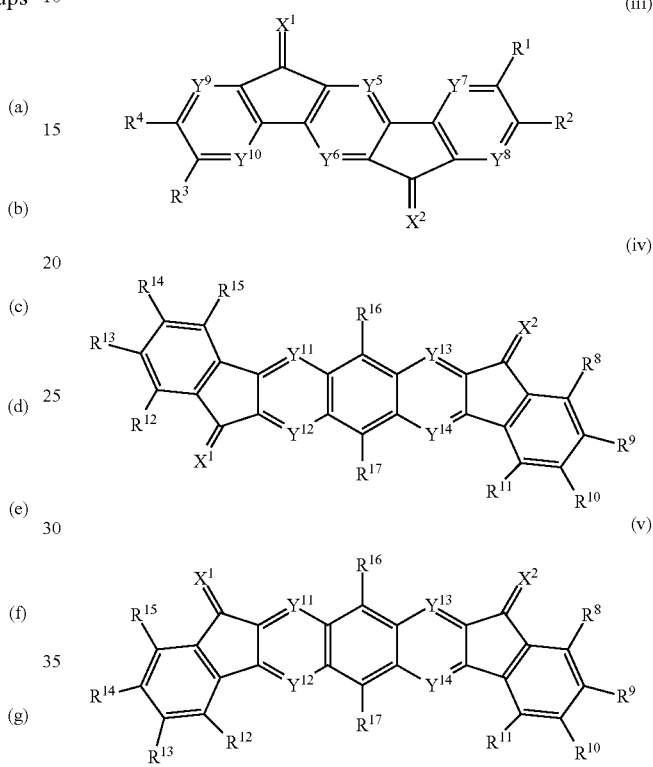

In formulae (iii), (iv), and (v), $X^1$ and $X^2$ are defined in the same manner as in formula (I); $R^1$ to $R^4$ and $R^8$ to $R^{17}$ are defined in the same manner as in $R^1$ to $R^4$ of formula (I), and $Y^5$ to $Y^{14}$ are defined in the same manner as in $Y^1$ to $Y^4$ of formula (I).

The present invention further relates to (2) a material for organic electroluminescence devices comprising the indenofluorenedione derivative represented by formula (I); and (3) an organic electroluminescence device comprising an anode, a cathode, and an organic thin layer between the anode and the cathode, wherein the organic thin layer comprises the material for organic electroluminescence device.

According to the present invention, an indenofluorenedione derivative which is excellent in the heat resistance and can be vapor-deposited on a substrate at moderate temperature and a material for organic electroluminescence devices comprising the indenofluorenedione derivative are provided. In addition, an organic electroluminescence device with a long lifetime which is driven at a low driving voltage is provided.

BRIEF DESCRIPTION OF DRAWINGS

FIG. 1 is a schematic cross-sectional view of an example of the organic EL device of the invention.

BEST MODE FOR CARRYING OUT THE INVENTION

Indenofluorenedione Derivative

The indenofluorenedione derivative of the invention is represented by the following formula (I):

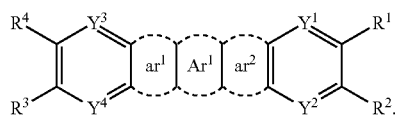

In formula (I), $Ar^1$ is a condensed ring having 6 to 24 nuclear carbon atoms or a heteroring having 6 to 24 nuclear atoms, preferably a condensed ring having 6 to 14 nuclear carbon atoms or a heteroring having 6 to 14 nuclear atoms. Examples of the condensed ring include benzene ring, naphthalene ring, fluorene ring, 9,9-dimethylfluorene ring, and 9,9-dioctylfluorene ring. Examples of the heteroring include pyrazine ring, pyridine ring, quinoxaline ring, thiophene ring, benzothiophene ring, dibenzothiophene ring, furan ring, benzofuran ring, dibenzofuran ring, phenanthroline ring, and naphthyridine ring. The condensed ring and the heteroring may be substituted by a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxyl group, a substituted or unsubstituted fluoroalkoxyl group, a substituted or unsubstituted aryloxy group, a substituted or unsubstituted aralkyloxy group, a substituted or unsubstituted amino group, or cyano group, which are also defined as $R^1$ to $R^4$ below.

In the present invention, "nuclear carbon atoms" means the carbon atoms forming a saturated ring, an unsaturated ring, or an aromatic ring, and "nuclear atoms" means the carbon atom(s) and the nitrogen atom(s) which form a heteroring (inclusive of a saturated ring, an unsaturated ring and an aromatic ring).

In formula (I), $R^1$ to $R^4$ may be the same or different and each independently represent hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxyl group, a substituted or unsubstituted fluoroalkoxyl group, a substituted or unsubstituted aryloxy group, a substituted or unsubstituted aralkyloxy group, a substituted or unsubstituted amino group, or cyano group. $R^1$ and $R^2$, and $R^3$ and $R^4$ may bond to each other to form a saturated or unsaturated divalent group which completes a ring.

Examples of the alkyl group include methyl group, ethyl group, n-propyl group, isopropyl group, n-butyl group, isobutyl group, tert-butyl group, and octyl group.

Examples of the cycloalkyl group include cyclopentyl group and cyclohexyl group.

Examples of the alkenyl group include vinyl group, propenyl group (inclusive of position isomers with respect to double bond), butenyl group (inclusive of position isomers with respect to double bond), and pentenyl group (inclusive of position isomers with respect to double bond).

Examples of the (substituted) aryl group include phenyl group, biphenyl group, naphthyl group, fluorophenyl group, trifluoromethylphenyl group, (trifluoromethyl)fluorophenyl group, trifluorophenyl group, bis(trifluoromethyl)phenyl group, (trifluoromethyl)difluorophenyl group, trifluoromethoxyphenyl group, and trifluoromethoxyfluorophenyl group.

Examples of the heterocyclic group include the residues of pyridine, pyrazine, furan, imidazole, benzimidazole, and thiophene.

Examples of the halogen atom include fluorine atom, chlorine atom, bromine atom, and iodine atom.

Examples of the fluoroalkyl group include trifluoromethyl group, pentafluoroethyl group, perfluorocyclohexyl group, and perfluoroadamantyl group.

Examples of the alkoxyl group include methoxy group and ethoxy group.

Examples of the fluoroalkoxyl group include trifluoromethoxy group, pentafluoroethoxy group, 2,2,2-trifluoroethoxy group, 2,2,3,3,3-pentafluoropropoxy group, 2,2,3,3-tetrafluoropropoxy group, and 1,1,1,3,3,3-hexafluoropropane-2-yloxy group Examples of the (substituted) aryloxy group include phenyloxy group, pentafluorophenyloxy group, and 4-trifluorophenyloxy group.

Examples of the (substituted) aralkyloxy group include benzyloxy group, pentafluorobenzyloxy group, and 4-trifluoromethylbenzyloxy group.

Examples of the (substituted) amino group include amino group, mono- or dimethylamino group, mono- or diethylamino group, and mono- or diphenylamino group.

The optional substituent of $R^1$ to $R^4$ may include the halogen atom, cyano group, the alkyl group, the aryl group, the fluoroalkyl group, the fluoroalkoxyl group, and the heterocyclic group, each mentioned above.

Unless otherwise noted, the optional substituent referred to herein by "substituted or unsubstituted" may include the halogen atom, cyano group, the alkyl group, the aryl group, the fluoroalkyl group, the fluoroalkoxyl group, and the heterocyclic group, each mentioned above.

As mentioned above, $R^1$ and $R^2$, and $R^3$ and $R^4$ may bond to each other to form a saturated or unsaturated divalent group which completes a ring, for example, benzene ring, naphthalene ring, pyrazine ring, pyridine ring, and furan ring.

At least one of $R^1$ to $R^4$ is preferably fluorine atom, a fluoroalkyl group, a fluoroalkoxyl group, cyano group, or an aryl group or heterocyclic group each having at least one group selected from fluorine, a fluoroalkyl group, a fluoroalkoxyl group, and cyano group. These substituents can enhance the electron accepting property, make the sublimation temperature moderate, or prevent the crystallization.

In formula (I), $ar^1$ and $ar^2$ may be the same or different and are independently represented by formula (i) or (ii):

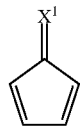

-continued

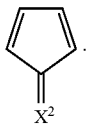
(ii)

In the above formulae, $X^1$ and $X^2$ may be the same or different and each represent any of the divalent groups (a) to (g). The groups (a) to (c) are particularly preferred in view of good heat resistance or easiness of synthesis.

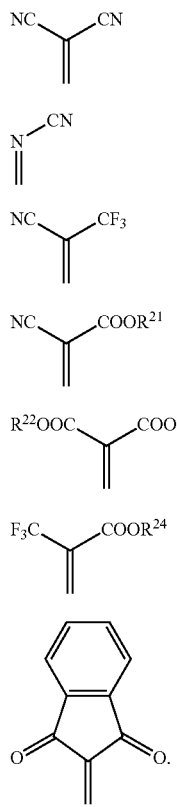

In the above formulae, $R^{21}$ to $R^{24}$ may be the same or different and each represent hydrogen atom, a substituted or unsubstituted fluoroalkyl group, a substituted or unsubstituted alkyl group, a substituted or unsubstituted cycloalkyl group, a substituted or unsubstituted aryl group, or a substituted or unsubstituted heterocyclic group. $R^{22}$ and $R^{23}$ may bond to each other to form a ring. Examples of the fluoroalkyl group, the alkyl group, the cycloalkyl group, the aryl group, and the heterocyclic group are the same as those for $R^1$ to $R^4$ mentioned above.

In formula (I), $Y^1$ to $Y^4$ may be the same or different and each represent —N=, —CH=, or —C($R^5$)=, wherein $R^5$ is defined in the same manner as $R^1$ to $R^4$. The adjacent groups of $R^1$ to $R^5$ may bond to each other to form a saturated or unsaturated divalent group which completes a ring.

At least one of $Y^1$ to $Y^4$ is preferably nitrogen atom (the same applies to $Y^{21}$ to $Y^{26}$ and $Y^{31}$ to $Y^{38}$ mentioned below). If at least one of $Y^1$ to $Y^4$ is nitrogen atom, the electron accepting property is enhanced, the heat resistance is high, or the crystallization is prevented.

The compounds represented by formulae (iii), (iv), and (v) are excluded from the compound represented by formula (I).

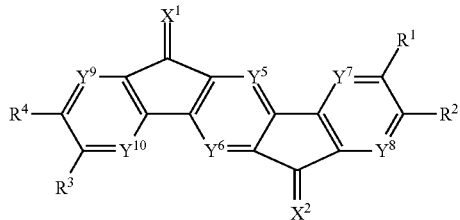
(iii)

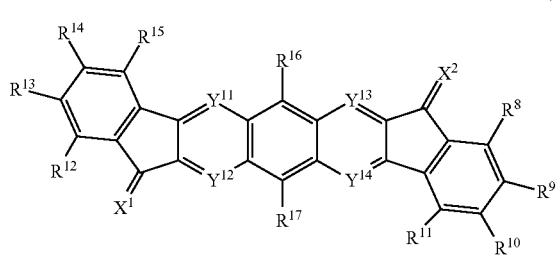
(iv)

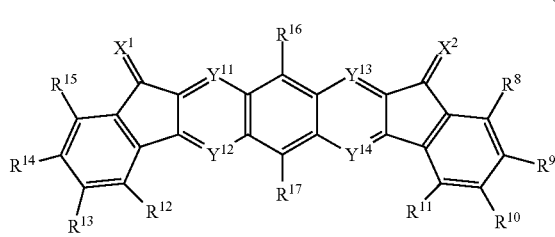
(v)

In formulae (iii), (iv), and (v), $X^1$ and $X^2$ are as defined in $X^1$ and $X^2$ of formula (I). $R^1$ to $R^4$ and $R^8$ to $R^{17}$ are as defined in $R^1$ to $R^4$ of formula (I). $Y^5$ to $Y^{14}$ are as defined in $Y^1$ to $Y^4$ of formula (I).

The indenofluorenedione derivative of formula (I) is preferably represented by the following formula (I-A) or (I-B):

(I-A)

(I-B)

In formula (I-A), each of $Ar^1$, etc. is as defined in the corresponding variable of formula (I). In formula (I-B), $Ar^2$ is as defined in $Ar^1$ of formula (I), $X^3$ and $X^4$ are as defined in $X^1$ and $X^2$ of formula (I), $Y^5$ to $Y^8$ are as defined in $Y^1$ to $Y^4$ of formula (I), and $R^1$ to $R^4$ are as defined in $R^1$ to $R^4$ of formula (I).

The indenofluorenedione derivative of formula (I) is more preferably represented by the following formulae (II) to (VII).

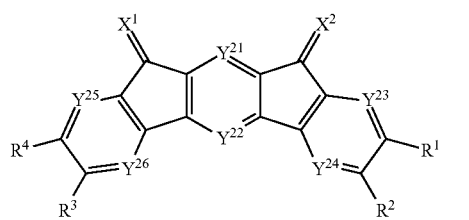
(II)

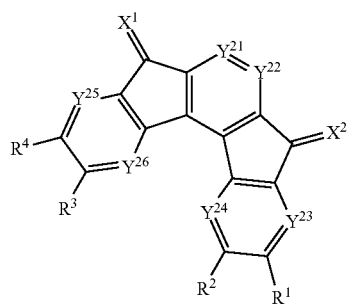
(III)

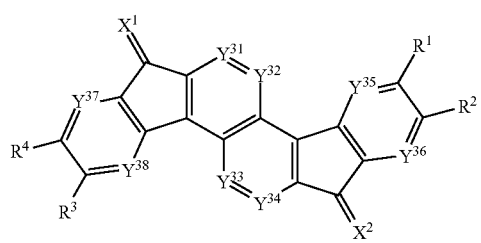
(IV)

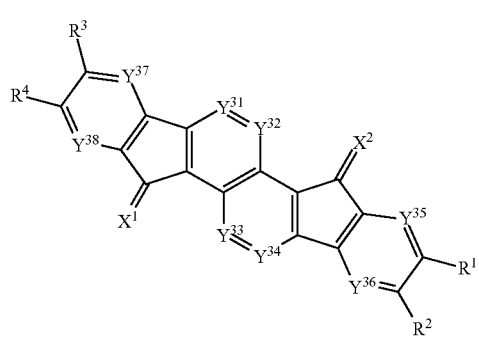
(V)

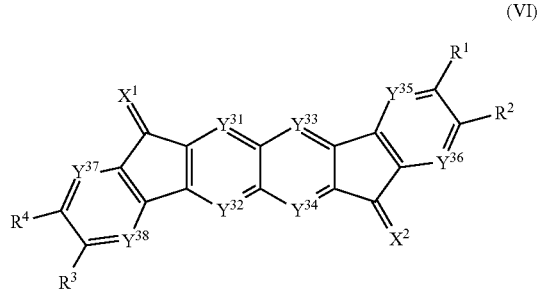
(VI)

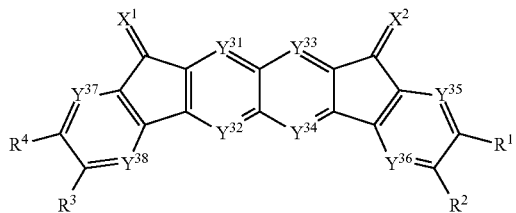
(VII)

In the above formulae, $X^1$, $X^2$, and $R^1$ to $R^4$ are as defined in $X^1$, $X^2$, and $R^1$ to $R^4$ of formula (I), respectively. $Y^{21}$ to $Y^{26}$ and $Y^{31}$ to $Y^{38}$ are as defined in $Y^1$ to $Y^4$ of formula (I).

The indenofluorenedione derivative of formula (I) is particularly preferably represented by the following formulae (I-a) to (I-l). The compounds represented by formulae (I-b), (I-d), (I-f), (I-h), (I-j), and (I-l) include isomers with respect to the orientations of the cyano groups in two cyanoimino groups. The compound of the invention is not limited to a specific isomer.

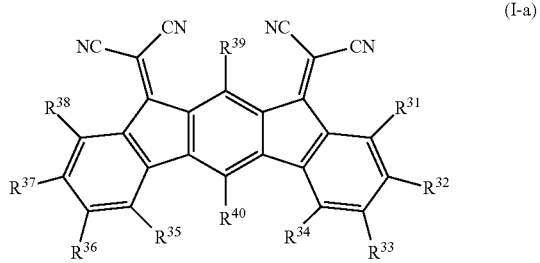
(I-a)

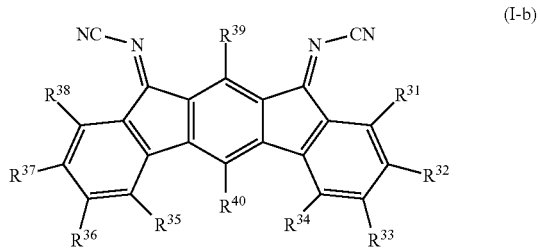
(I-b)

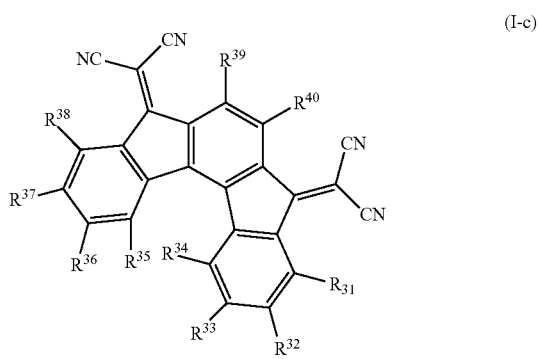
(I-c)

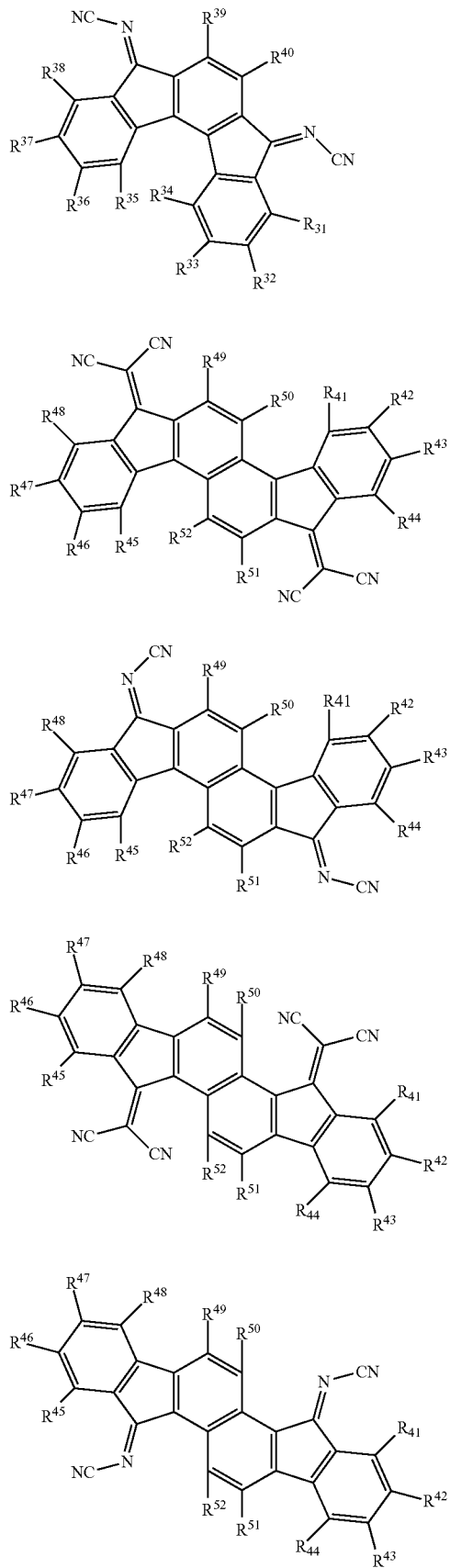
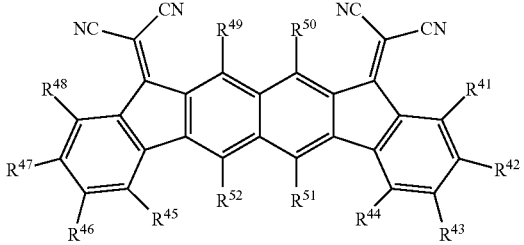
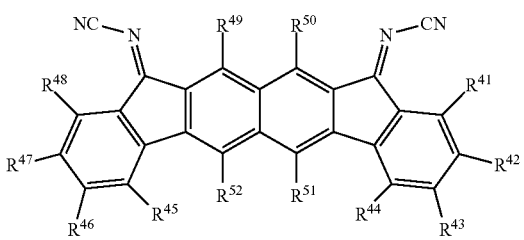
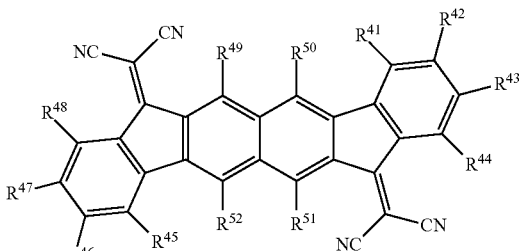
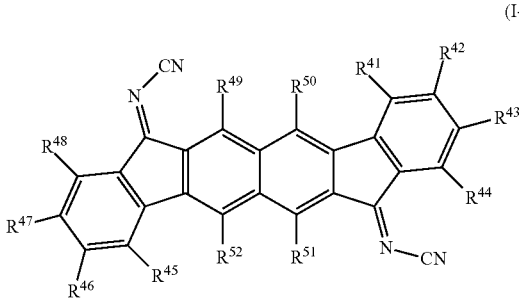

In the above formulae, $R^{31}$ to $R^{52}$ are as defined in $R^1$ to $R^4$ of formula (I). The adjacent groups of $R^{31}$ to $R^{52}$ may bond to each other to form a saturated or unsaturated divalent group which completes a ring. Particularly, at least one of $R^{31}$ to $R^{52}$ is preferably fluorine atom, a fluoroalkyl group, a fluoroalkoxyl group, cyano group, or an aryl group or heterocyclic group each having at least one group selected from fluorine, a fluoroalkyl group, a fluoroalkoxyl group, and cyano group.

With the structures described above, the indenofluorenedione derivative of the invention has electron accepting property and good heat resistance, and further has a sublimation temperature of about 200° C. or higher to enable the purification by sublimation, giving a highly pure compound. In addition, an organic EL device employing the indenofluorenedione derivative can be driven at a lower voltage and has an improved lifetime. Since the sublimation temperature is about 200° C. or higher, the indenofluorenedione derivative does not scatter into a film-forming apparatus for vapor deposition during the production of devices, and therefore, does not contaminate the film-forming apparatus and the organic EL devices being produced. Therefore, the indenofluorenedione derivative of the invention is suitable as a material for organic EL devices, particularly, a hole injecting material.

Examples of the indenofluorenedione derivative are described below, although not limited thereto.
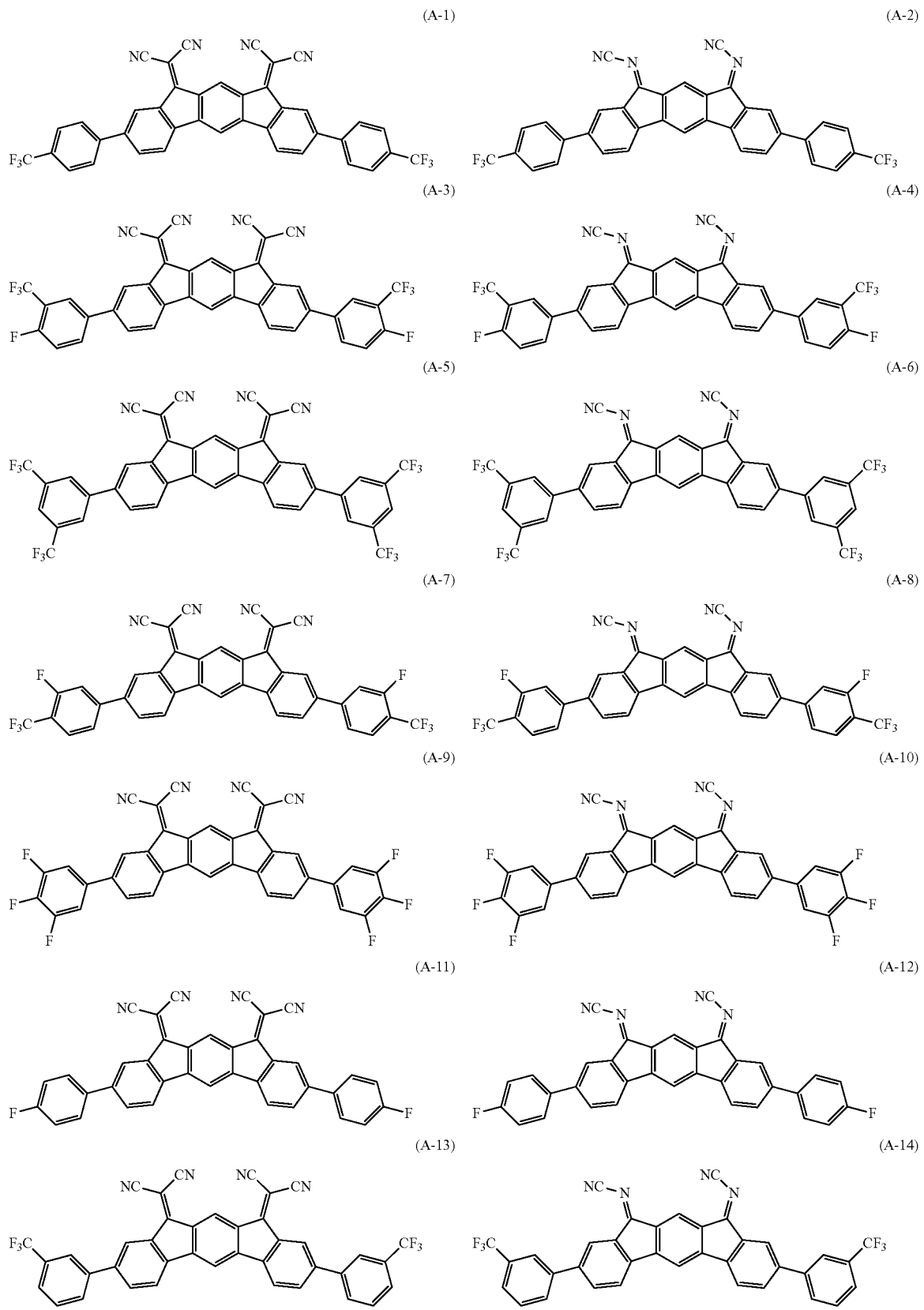

-continued
(A-15)
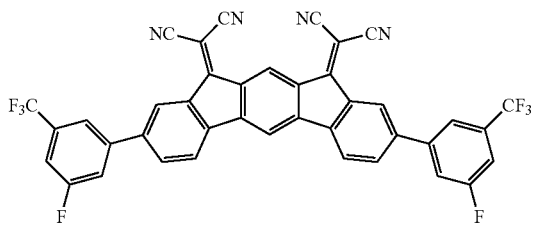
(A-16)
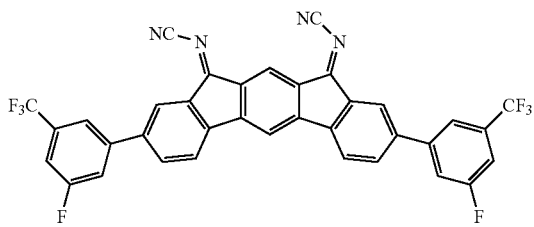
(A-17)
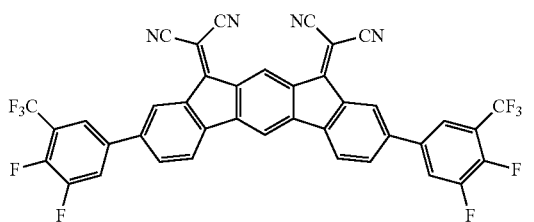
(A-18)
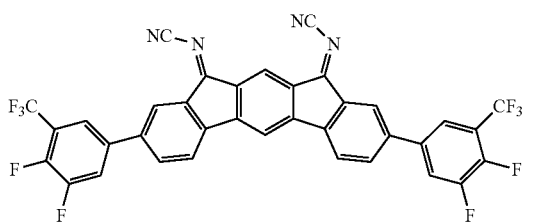
(A-19)
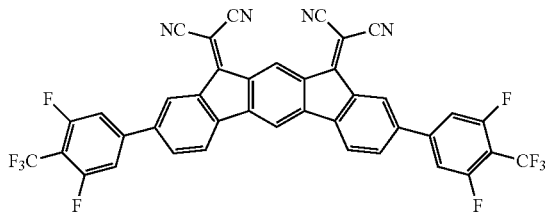
(A-20)
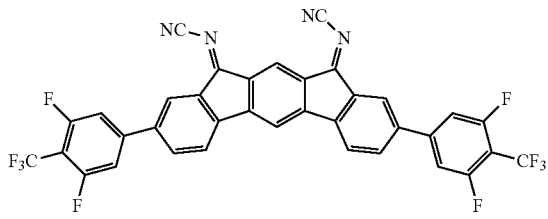
(A-21)
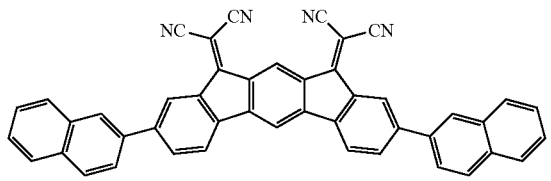
(A-22)
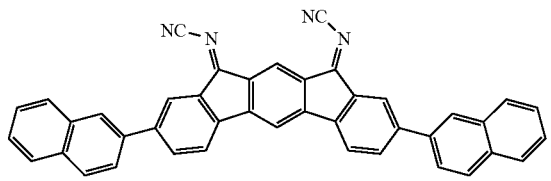
(A-23)
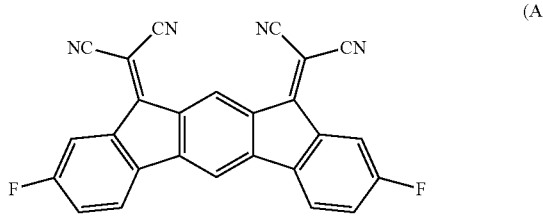
(A-24)
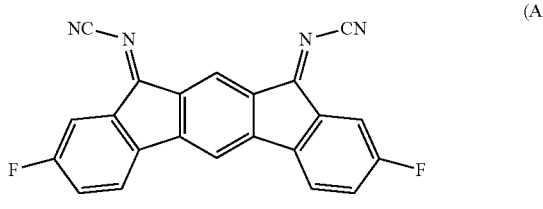
(A-25)
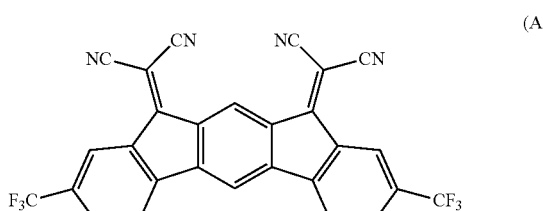
(A-26)
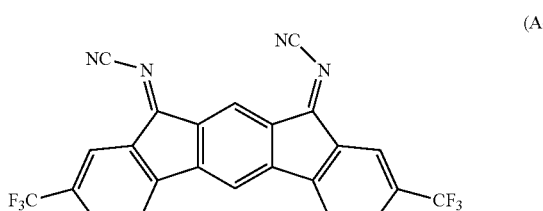
(A-27)
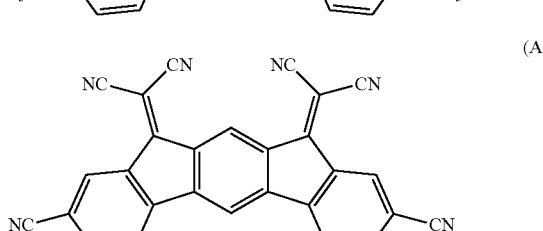
(A-28)
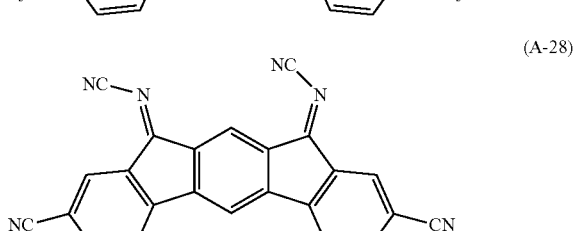

-continued
(A-29)
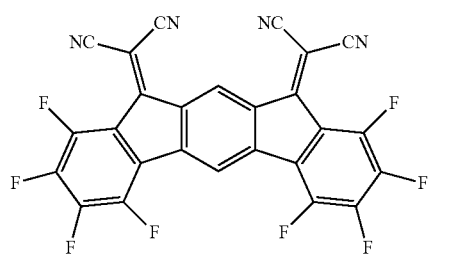
(A-30)
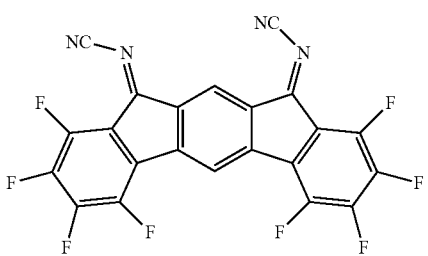
(A-31)
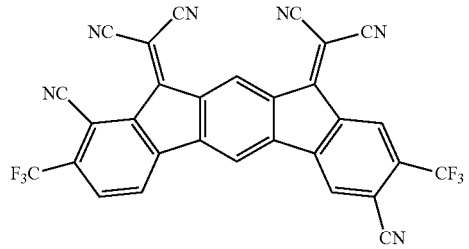
(A-32)
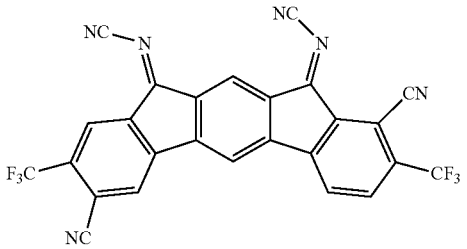
(A-33)
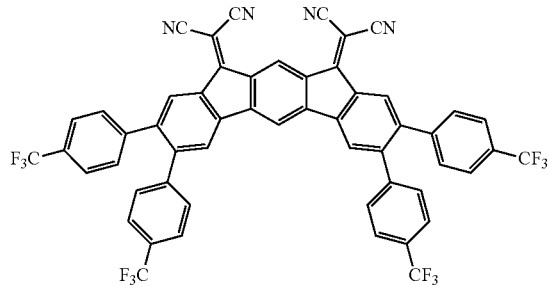
(A-34)
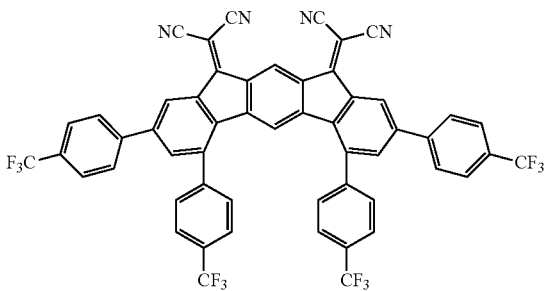
(A-35)
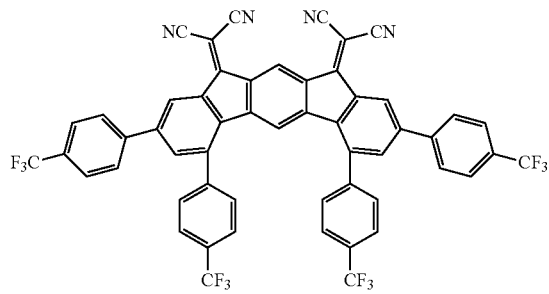
(A-36)
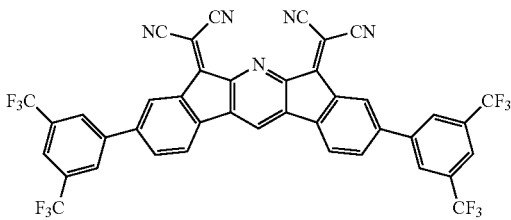
(A-37)
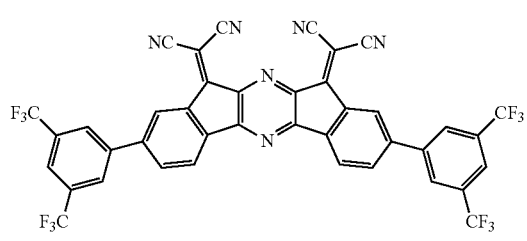
(A-38)
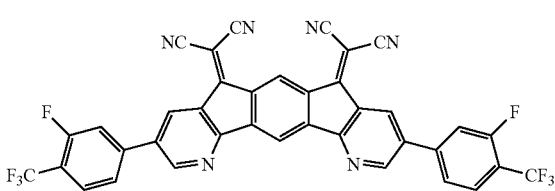
(A-39)
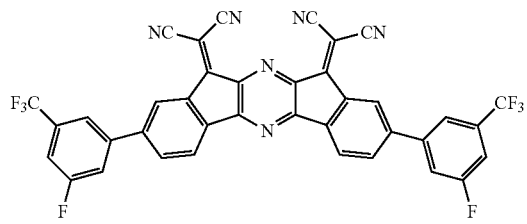
(A-40)
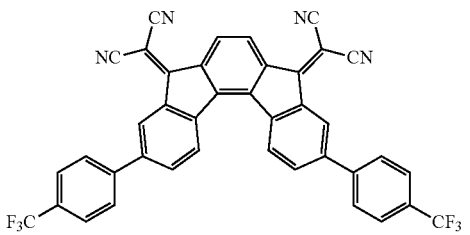

-continued
(A-41)
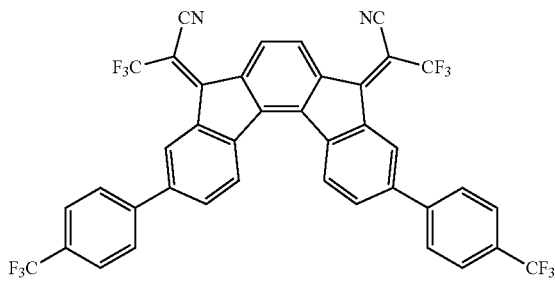
(A-42)
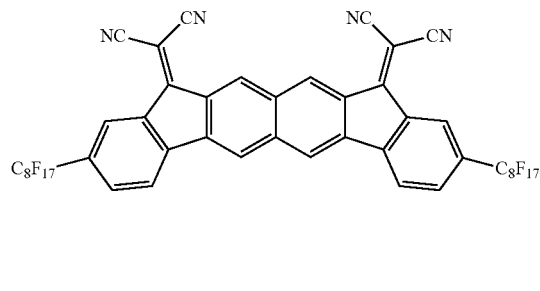
(A-43)
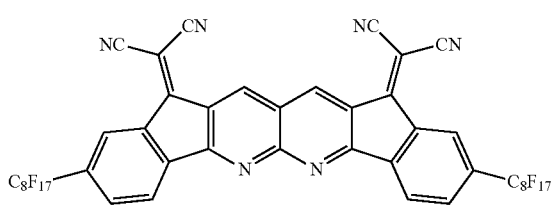
(A-44)
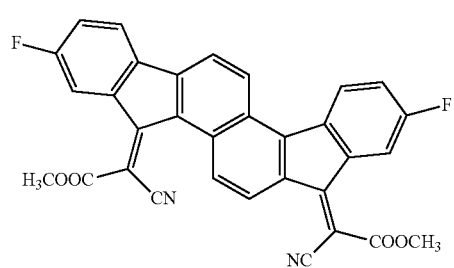
(A-45)
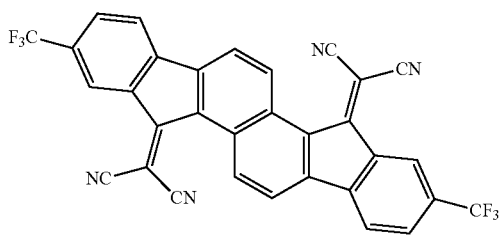
(A-46)
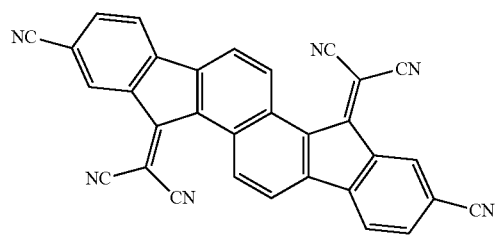
(A-47)
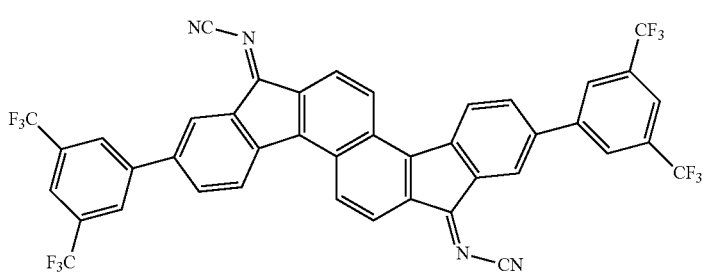
(A-48)
(A-49)
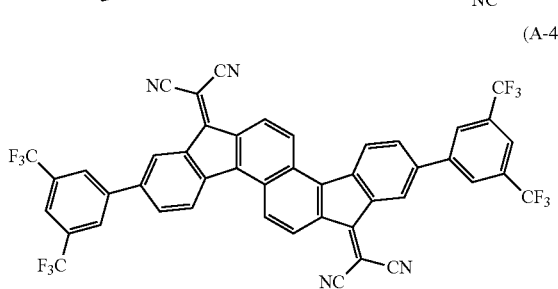
(A-50)
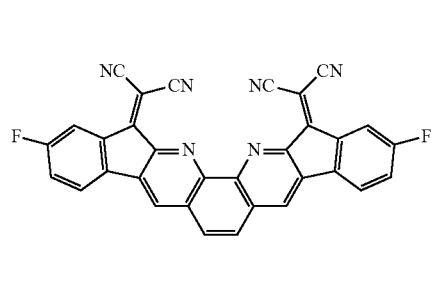

-continued
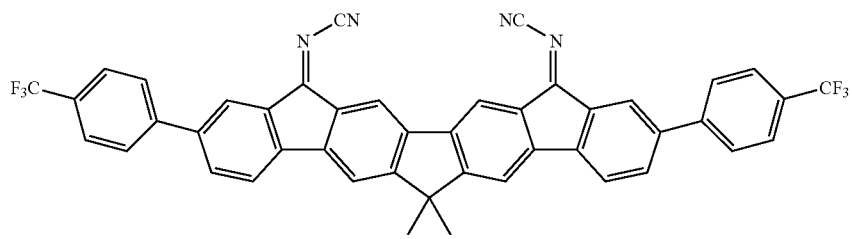
(A-51)
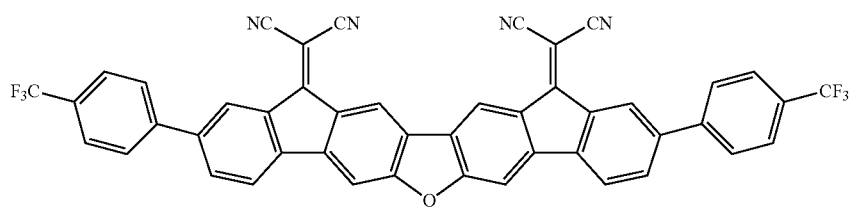
(A-52)
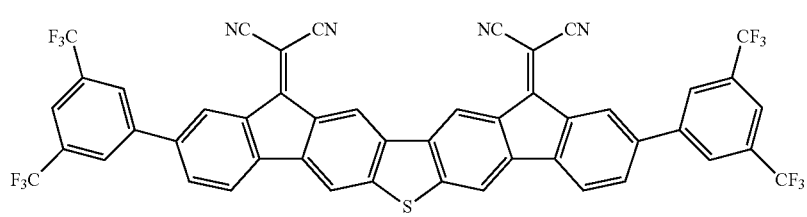
(A-53)
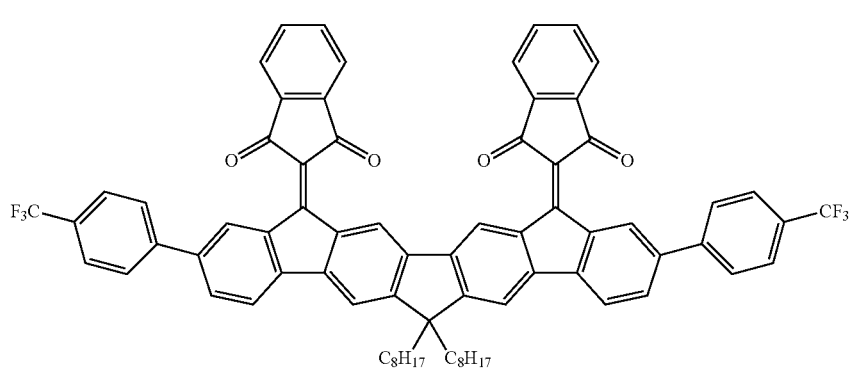
(A-54)
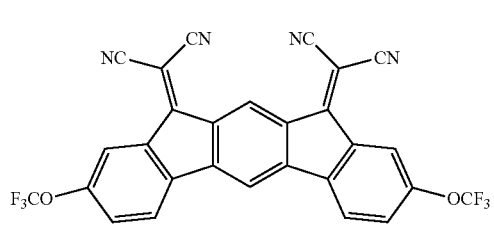
(A-55)
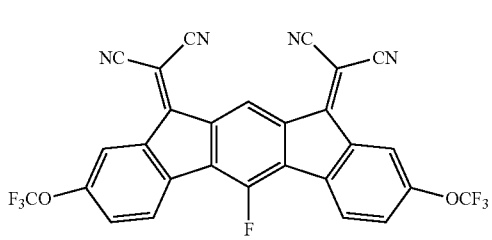
(A-56)
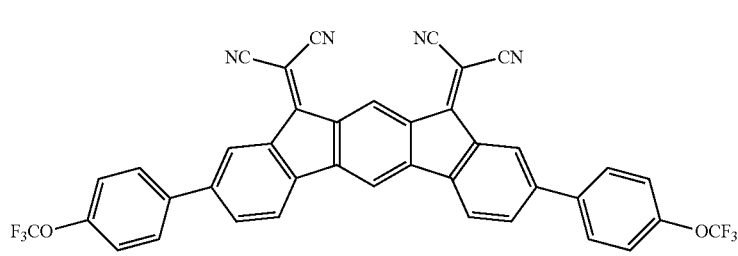
(A-57)

-continued
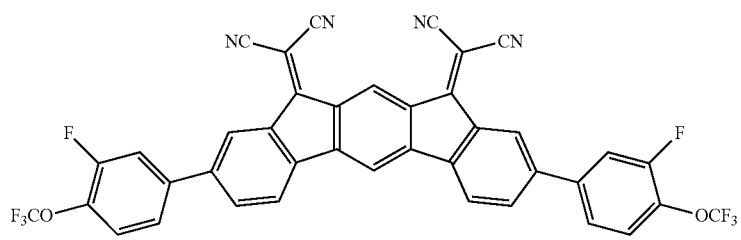
(A-58)
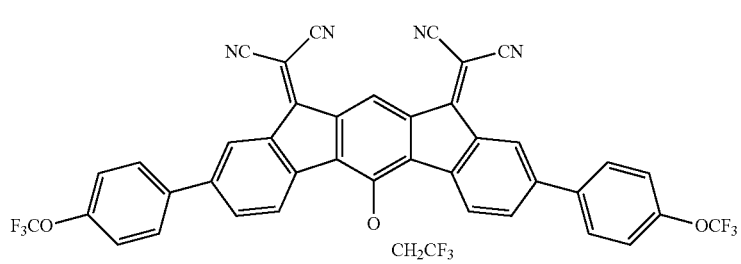
(A-59)
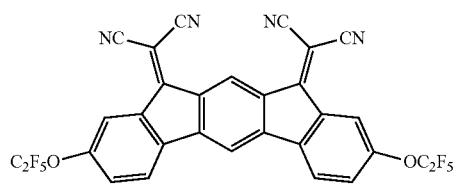
(A-60)
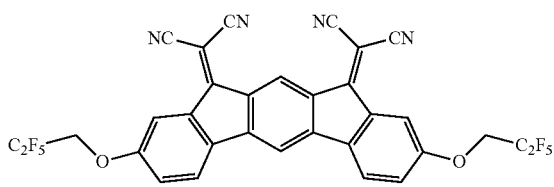
(A-61)
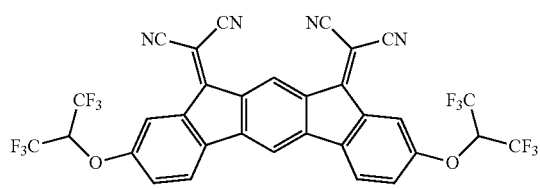
(A-62)
(A-63)
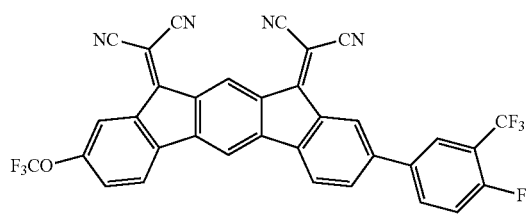
(A-64)
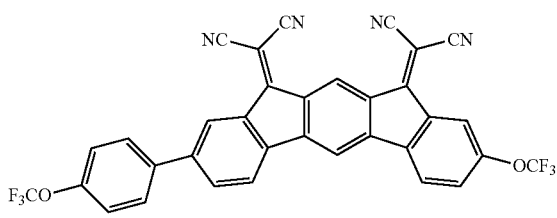
(A-65)
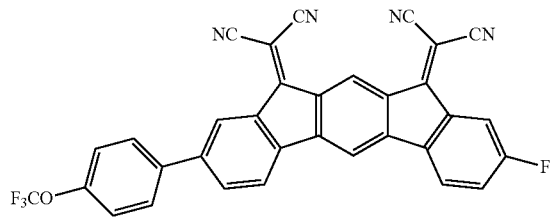
(A-66)
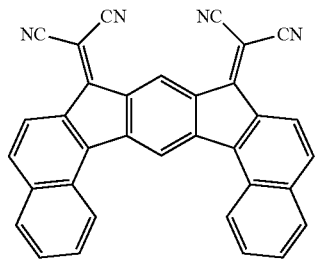
(A-67)

-continued
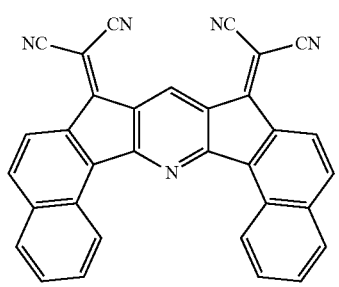
(A-68)
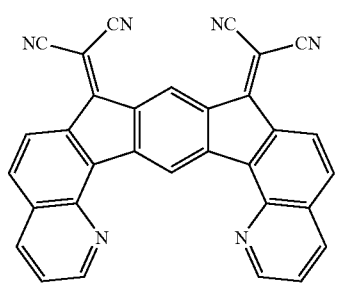
(A-69)
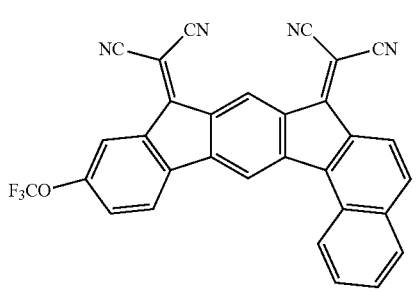
(A-70)
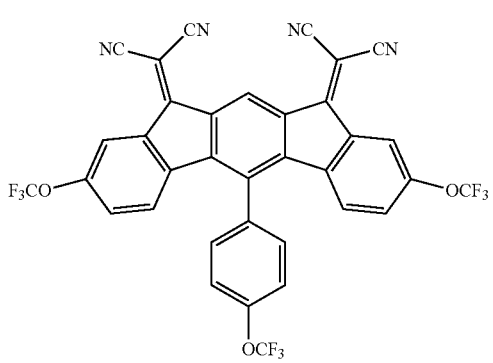
(A-71)
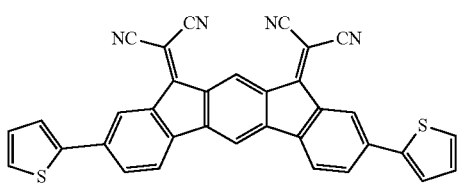
(A-72)
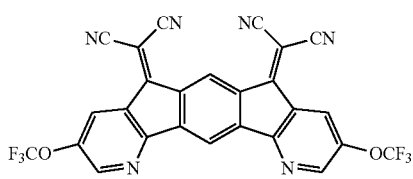
(A-73)
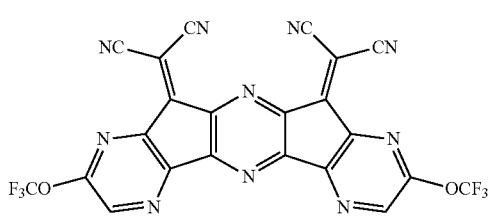
(A-74)
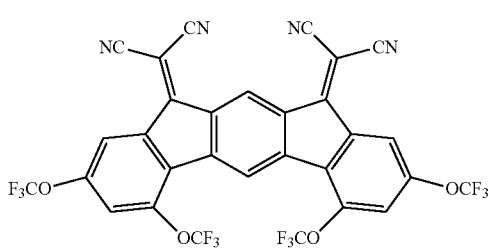
(A-75)
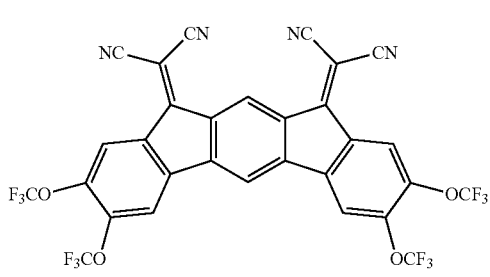
(A-76)
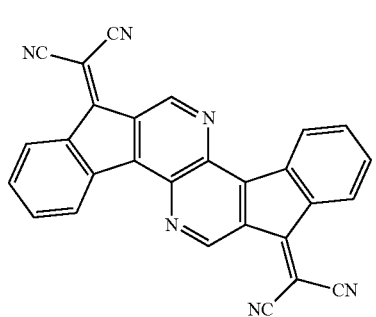
(A-77)

(A-78)
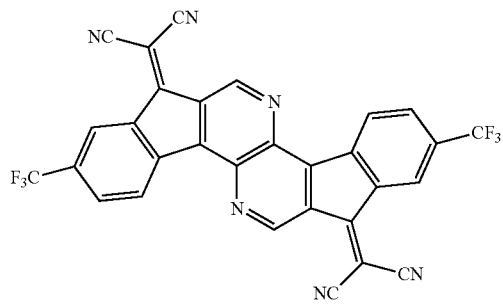

(A-79)
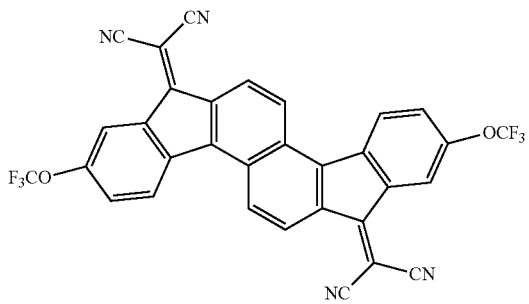

(A-80)
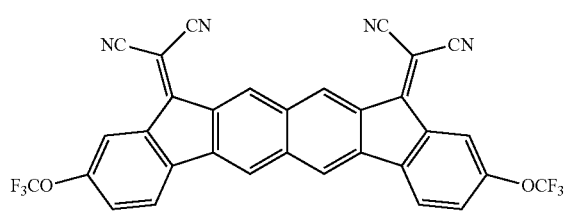

In the production of the indenofluorenedione derivative of the invention, an indenofluorenedione (I) is first synthesized according to Scheme 1 with reference to the synthesis methods described in Chemische Berichte, 1956, vol. 89, p 2799, Journal of Organic Chemistry, 2001, vol. 66, p 7666, and Japanese Patent 3098330. The indenofluorenedione (I) is converted to a corresponding dicyanomethylene derivative or cyanoimino derivative (II) by a method shown in Scheme 2 (details of synthesis conditions, etc. are found, for example, in Liebigs Ann. Chem. 1986, p 142). The obtained crystals are sublimed for purification to remove impurities, thereby providing good performance for improving lifetime, etc. of an organic EL device employing the resulting compound.

Scheme 1

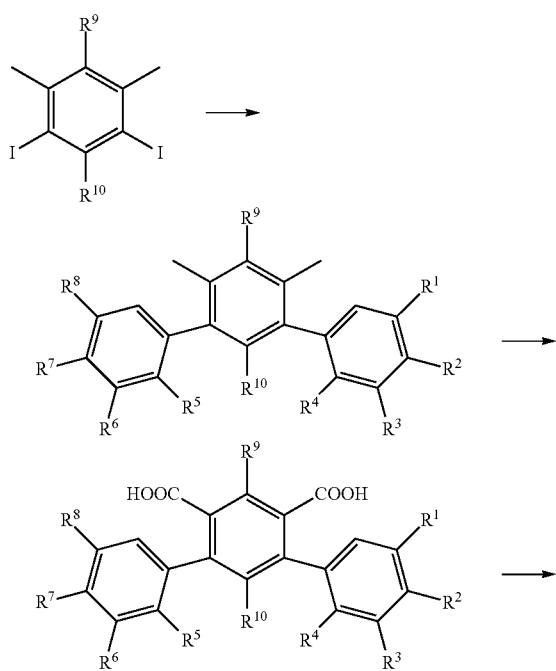

Scheme 2

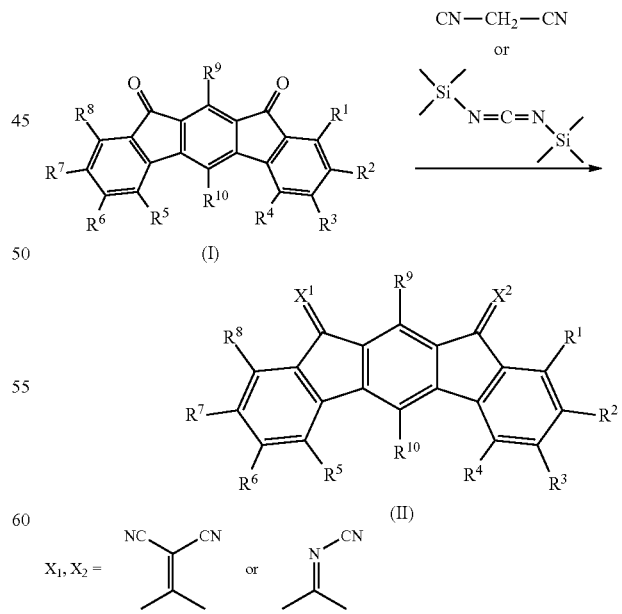

In the above structural formulae, the valuables are as defined in formula (I).

Material for Organic Electroluminescence Devices

The material for organic EL devices of the invention contains at least one kind of the indenofluorenedione derivative of the invention and has a reduction potential of preferably −1.0 V or more (vs Fc+/Fc), more preferably −0.8 V or more (vs Fc$^+$/Fc) when measured in an acetonitrile solution, wherein Fc is ferrocene.

If the reduction potential is −1.0 V or more, the electron accepting property is increased. Increased electron accepting property makes the electron transfer between the material and the anode made of ITO or other material having a work function lower than that of ITO easier and makes the HOMO level of a hole transporting material and the LUMO level of an electron accepting compound close, thereby making the injection of holes easier.

Organic Electroluminescence Device

The organic EL device of the invention will be described below.

The organic EL device comprises an anode, a cathode and an organic thin layer between the anode and the cathode. The organic thin layer contains the material for organic electroluminescence device of the invention.

FIG. 1 is a schematic cross-sectional view of an embodiment of the organic EL devices according to the invention.

The organic EL device 1 is composed of a substrate (not shown) and an anode 10, a hole injecting layer 20, a hole transporting layer 30, a light emitting layer 40, an electron transporting layer 50, and a cathode 60 which are laminated on the substrate in this order. The organic thin layer (also referred to as "organic layer") has a laminated structure composed of the hole injecting layer 20, the hole transporting layer 30, the light emitting layer 40, and the electron transporting layer 50. In the organic EL device having such a layered structure, it is preferred that at least the hole injecting layer 20 contains the material for organic EL devices of the invention. With such a structure, the organic EL device can be driven at lower voltage and a long lifetime is achieved.

An organic layer other than the hole injecting layer may contain the material for organic EL devices of the invention alone or in combination with the material for each layer which will be described below.

The content of the material for organic EL devices in the hole injecting layer is preferably 1 to 100 mol % and more preferably 3 to 100 mol %.

The material for organic EL devices of the invention can be applied to devices having a layered structure different from that of the above embodiment. For example, the material for organic EL devices may be included in each organic layer, such as the light emitting layer, of the devices having the following layered structures (1) to (15):

(1) anode/light emitting layer/cathode,
(2) anode/hole transporting layer/light emitting layer/cathode,
(3) anode/light emitting layer/electron transporting layer/cathode,
(4) anode/hole transporting layer/light emitting layer/electron transporting layer/cathode,
(5) anode/hole transporting layer/light emitting layer/adhesion improving layer/cathode,
(6) anode/hole injecting layer/hole transporting layer/light emitting layer/electron transporting layer/cathode (FIG. 1),
(7) anode/hole transporting layer/light emitting layer/electron transporting layer/electron injecting layer/cathode,
(8) anode/hole injecting layer/hole transporting layer/light emitting layer/electron transporting layer/electron injecting layer/cathode,
(9) anode/insulating layer/hole transporting layer/light emitting layer/electron transporting layer/cathode,
(10) anode/hole transporting layer/light emitting layer/electron transporting layer/insulating layer/cathode,
(11) anode/inorganic semiconductor layer/insulating layer/hole transporting layer/light emitting layer/insulating layer/cathode,
(12) anode/insulating layer/hole transporting layer/light emitting layer/electron transporting layer/insulating layer/cathode,
(13) anode/hole injecting layer/hole transporting layer/light emitting layer/electron transporting layer/insulating layer/cathode,
(14) anode/insulating layer/hole injecting layer/hole transporting layer/light emitting layer/electron transporting layer/electron injecting layer/cathode, and
(15) anode/insulating layer/hole injecting layer/hole transporting layer/light emitting layer/electron transporting layer/electron injecting layer/insulating layer/cathode.

Of the above, preferred are the layered structures (4), (6), (7), (8), (12), (13), and (15).

The members for constituting the organic EL device of the invention will be described below.

Substrate

The organic EL device of the invention is formed on a light-transmissive substrate. The light-transmissive substrate serves as a support for the organic EL device and preferably a flat substrate having a transmittance of 50% or more to 400 to 700 nm visible light.

Examples of the substrate include a plate of glass, such as soda-lime glass, barium-strontium-containing glass, lead glass, aluminosilicate glass, borosilicate glass, barium borosilicate glass, and quartz; and a plate of polymer, such as polycarbonate, acrylic resin, polyethylene terephthalate, polyether sulfide, and polysulfone.

When getting the emitted light from the side opposite to the substrate, the substrate is not needed to be light-transmissive.

Anode

The anode of the organic EL device injects holes to the hole transporting layer or the light emitting layer. If needed to be transparent, the anode is made from indium tin oxide alloy (ITO), tin oxide (NESA), indium zinc oxide alloy (IZO), gold, silver, platinum, or cupper. If a reflective electrode which is not needed to be transparent is intended, the anode can be made from, in addition to the materials mentioned above, metal or alloy of aluminum, molybdenum, chromium and nickel.

Even when the hole injecting layer comprising the material for organic EL devices of the invention is combined with an anode of low work function (for example, 5.0 eV or less), the electron transfer occurs and the injection property is good.

The above materials may be used alone. Alloys of the above materials and the material added with other elements are also usable.

The anode is formed by making the electrode material into a thin film by a vapor deposition method or a sputtering method. When getting the emitted light from the light emitting layer through the anode, the transmittance of anode to emitted light is preferably 10% or more. The sheet resistance of anode is preferably several hundreds Ω/□ or less. The film thickness of anode depends upon the kind of material and generally 10 nm to 1 μm, preferably 10 to 200 nm.

Light Emitting Layer

The light emitting layer of organic EL device combines the following functions (1) to (3):
(i) Injection function: allowing holes to be injected from the anode or hole injecting layer, and allowing electrons to be injected from the cathode or electron injecting layer, by the action of electric field;
(ii) Transporting function: transporting the injected charges (holes and electrons) by the force of electric field; and
(iii) Emission function: providing a zone for recombination of electrons and holes to cause emission.

The light emitting layer may be different in the hole injection ability and the electron injection ability, and also may be different in the hole transporting ability and the electron transporting ability each being expressed by mobility, although it is preferred to transport either of hole or electron dominantly.

For example, a known process such as a vapor deposition process, a spin coating process, or LB process is applicable to the formation of the light emitting layer. The light emitting layer is particularly preferably a molecular deposit film. The molecular deposit film is a thin film formed by depositing a vaporized material or a film formed by solidifying a material in the state of solution or liquid. The molecular deposit film can be distinguished from a thin film formed by LB process (molecular build-up film) by the differences in the assembly structures and higher order structures and the functional difference due to the structural differences.

In addition, the light emitting layer can be also formed by making a solution of a binder, such as a resin, and its material in a solvent into a thin film by a spin coating method.

The light emitting materials usable in the light emitting layer includes, for example, anthracene, naphthalene, phenanthrene, pyrene, tetracene, coronene, chrysene, fluorescein, perylene, phthaloperylene, naphthaloperylene, perinone, phthaloperinone, naphthaloperinone, diphenylbutadiene, tetraphenylbutadiene, coumarin, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinylanthracene, diaminecarbazol, pyran, thiopyran, polymethyne, merocyanine, imidazol chelate oxinoid compound, quinacridone, rubrene and fluorescent dye, although not limited thereto.

Examples of the host material for use in the light emitting layer include the compounds represented by the following formulae (i) to (ix).

Asymmetric Anthracene Represented by Formula (i):

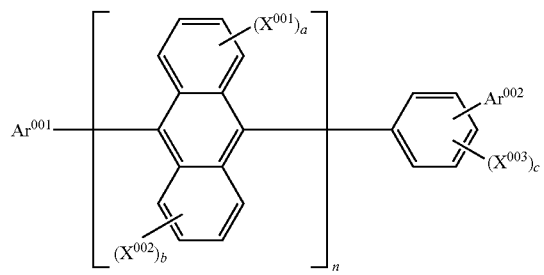

wherein $Ar^{001}$ is a substituted or unsubstituted condensed aromatic group having 10 to 50 nuclear carbon atoms; $Ar^{002}$ is a substituted or unsubstituted aromatic group having 6 to 50 nuclear carbon atoms; $X^{001}$ to $X^{003}$ are each independently a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, carboxyl group, a halogen atom, cyano group, nitro group, or hydroxy group; a, b and c are each an integer of 0 to 4; n is an integer of 1 to 3, and when n is 2 or more, the anthracene structures in [ ] may be the same or different.

Asymmetric Monoanthracene Derivative Represented by Formula (ii):

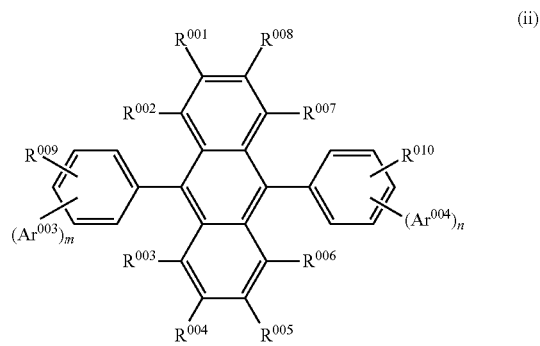

wherein $Ar^{003}$ and $Ar^{004}$ are each independently a substituted or unsubstituted aromatic ring group having 6 to 50 nuclear carbon atoms; m and n are each an integer of 1 to 4, with the proviso that when m=n=1 and the bonding positions of $Ar^{003}$ and $Ar^{004}$ to the benzene rings are bilaterally symmetric to each other, $Ar^{003}$ is different from $Ar^{004}$, and when m or n is an integer of 2 to 4, m is different from n; and $R^{001}$ to $R^{010}$ are each independently hydrogen atom, a substituted or unsubstituted aromatic ring group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a substituted or unsubstituted silyl group, carboxyl group, a halogen atom, cyano group, nitro group, or hydroxy group.

Asymmetric Pyrene Derivative Represented by Formula (iii);

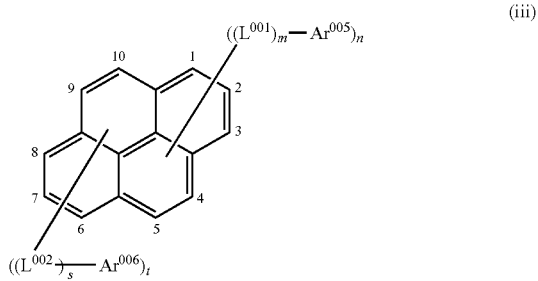

(iii)

wherein $Ar^{005}$ and $Ar^{006}$ are each a substituted or unsubstituted aromatic group having 6 to 50 nuclear carbon atoms; $L^{001}$ and $L^{002}$ are each a substituted or unsubstituted phenylene group, a substituted or unsubstituted naphthalenylene group, a substituted or unsubstituted fluorenylene group, or a substituted or unsubstituted dibenzosilolylene group; and m is an integer of 0 to 2, n is an integer of 1 to 4, s is an integer of 0 to 2, and t is an integer of 0 to 4. $L^{001}$ and $Ar^{005}$ bond to pyrene at any of 1- to 5-positions, and $L^{002}$ and $Ar^{006}$ bond to pyrene at any of 6- to 10-positions.

Asymmetric Anthracene Derivative Represented by Formula (iv);

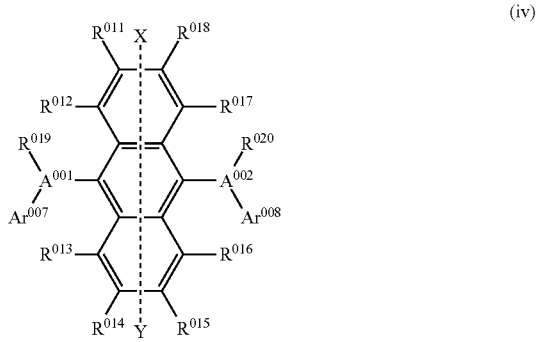

(iv)

wherein $A^{001}$ and $A^{002}$ are each independently a substituted or unsubstituted condensed aromatic ring group having 10 to 20 nuclear carbon atoms; $Ar^{007}$ and $Ar^{008}$ are each independently hydrogen atom or a substituted or unsubstituted aromatic ring group having 6 to 50 nuclear carbon atoms; $R^{011}$ to $R^{020}$ are each independently hydrogen atom, a substituted or unsubstituted aromatic ring group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a substituted or unsubstituted silyl group, carboxyl group, a halogen atom, cyano group, nitro group, or hydroxy group; and each of $Ar^{007}$, $Ar^{008}$, $R^{019}$ and $R^{020}$ may represent two or more groups and adjacent pair of groups may form a saturated or unsaturated ring structure, with the proviso that the groups bonding to 9- and 10-positions of the central anthracene ring are not bilaterally symmetric with respect to the axis X—Y.

Anthracene Derivative Represented by Formula (v):

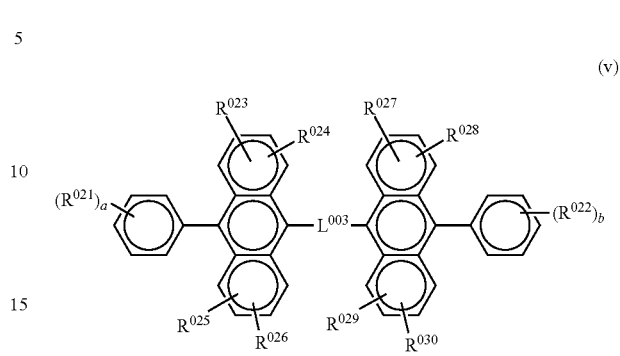

(v)

wherein $R^{021}$ to $R^{030}$ are each independently hydrogen atom, an alkyl group, a cycloalkyl group, a substituted or unsubstituted aryl group, an alkoxyl group, an aryloxy group, an alkylamino group, an alkenyl group, an arylamino group, or a substituted or unsubstituted heterocyclic group; a and b are each an integer of 1 to 5, when a and b are 2 or more, $R^{021}$ groups and $R^{022}$ groups may be the same or different, respectively, and $R^{021}$ groups and $R^{022}$ groups may bond to each other to form a ring, and $R^{023}$ and $R^{024}$, $R^{025}$ and $R^{026}$, $R^{027}$ and $R^{028}$, and $R^{029}$ and $R^{030}$ may bond to each other to form a ring; $L^{003}$ is a single bond, —O—, —S—, —N(R)— wherein R is an alkyl group or a substituted or unsubstituted aryl group, an alkylene group, or an arylene group.

Anthracene Derivative Represented by Formula (vi):

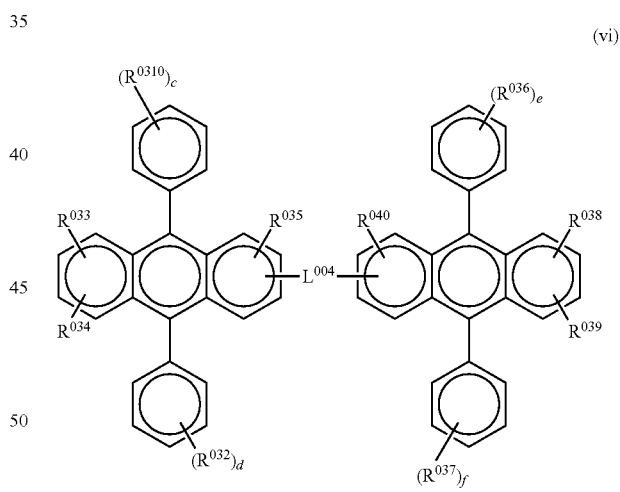

(vi)

wherein $R^{031}$ to $R^{040}$ are each independently hydrogen atom, an alkyl group, a cycloalkyl group, an aryl group, an alkoxyl group, an aryloxy group, an alkylamino group, an arylamino group, or a substituted or unsubstituted heterocyclic group; c, d, e and f are each an integer of 1 to 5, when c, d, e and f are 2 or more, $R^{031}$ groups, $R^{032}$ groups, $R^{036}$ groups and $R^{037}$ groups may be the same or different, respectively, and $R^{031}$ groups, $R^{032}$ groups, $R^{033}$ groups and $R^{037}$ groups may bond to each other to form a ring, and $R^{033}$ and $R^{034}$ and $R^{038}$ and $R^{040}$ may bond to each other to form a ring; and $L^{004}$ is a single bond, —O—, —S—, —N(R)— wherein R is an alkyl group or a substituted or unsubstituted aryl group, an alkylene group, or an arylene group.

Spirofluorene Derivative Represented by Formula (vii):

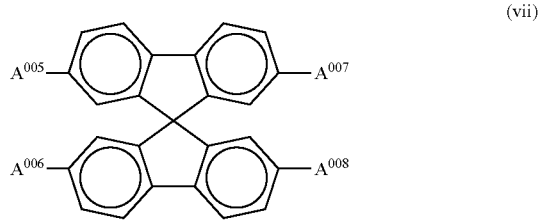

wherein $A^{005}$ to $A^{008}$ are each independently a substituted or unsubstituted biphenylyl group or a substituted or unsubstituted naphthyl group.

Condensed Ring-Containing Compound Represented by Formula (viii):

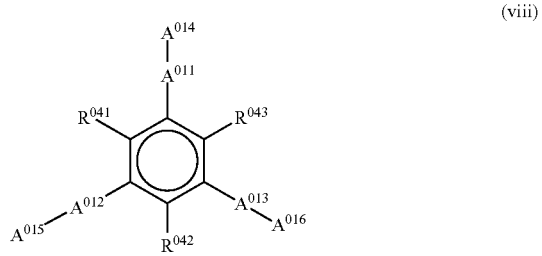

wherein $A^{011}$ to $A^{013}$ are each independently a substituted or unsubstituted arylene group having 6 to 50 nuclear carbon atoms; $A^{014}$ to $A^{016}$ are each independently hydrogen atom or a substituted or unsubstituted aryl group having 6 to 50 nuclear carbon atoms; $R^{041}$ to $R^{043}$ are each independently hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, nitro group, cyano group, an ester group having 1 to 6 carbon atoms, or a halogen atom; and at least one of $A^{011}$ to $A^{016}$ is a tri- or more cyclic condensed aromatic group.

Fluorene Compound Represented by Formula (ix):

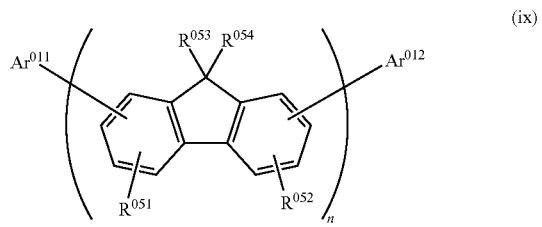

wherein $R^{051}$ and $R^{052}$ are each hydrogen atom, a substituted or unsubstituted alkyl group, a substituted or unsubstituted aralkyl group, a substituted or unsubstituted aryl group, a substituted or unsubstituted heterocyclic group, a substituted amino group, cyano group, or a halogen atom; $R^{051}$ groups and $R^{052}$ groups each bonding to different fluorene groups may be the same or different; $R^{051}$ and $R^{052}$ bonding to the same fluorene group may be the same or different; $R^{053}$ and $R^{051}$ are each hydrogen atom, a substituted or unsubstituted alkyl group, a substituted or unsubstituted aralkyl group, a substituted or unsubstituted aryl group, or a substituted or unsubstituted heterocyclic group; $R^{053}$ groups and $R^{054}$ groups each bonding to different fluorene groups may be the same or different; $R^{053}$ and $R^{054}$ bonding to the same fluorene group may be the same or different; $Ar^{011}$ and $Ar^{012}$ are each a substituted or unsubstituted condensed polycyclic aromatic group having 3 or more benzene rings or a substituted or unsubstituted condensed polyheterocyclic group having a benzene ring and a hetero ring three or more in total and bonding to the fluorene group via carbon; $Ar^{011}$ and $Ar^{012}$ may be the same or different; and n is an integer of 1 to 10.

Of the above host materials, preferred are the anthracene derivatives, more preferred are the monoanthracene derivatives, and particularly preferred are the asymmetric anthracenes.

In addition, a phosphorescent compound may be used as the light emitting material. When the phosphorescent compound is used, the host material is preferably a compound containing a carbazole ring. A compound capable of emitting light from triplet exciton is used as the dopant. The dopant is not particularly limited as long as it emits light from triplet exciton, and preferably a metal complex containing at least one metal selected from the group consisting of Ir, Ru, Pd, Pt, Os and Re, more preferably a porphyrin metal complex or an orthometalated complex.

A host suitable for phosphorescence, which comprises a compound containing a carbazole ring, is a compound capable of causing the emission of phosphorescent compound by transferring energy from its excited state to the phosphorescent compound. The host compound is not limited as long as it is capable of transferring the exciton energy to the phosphorescent compound and may be appropriately selected according to the purpose. The host compound may have any group such as a hetero ring in addition to the carbazole ring.

Specific examples of the host compound include a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene compound, a porphyrin-based compound, an anthraquinodimethane derivative, an anthrone derivative, a diphenylquinone derivative, a thiopyran dioxide derivative, a carbodiimide derivative, a fluorenylidene methane derivative, a distyrylpyrazine derivative, a heterocyclic tetracarboxylic anhydride such as a naphthaleneperylene, a phthalocyanine derivative, a metal complex polysilane compound such as a metal complex of 8-quinolinol derivative and a metal complex having a ligand such as metallophthalocyanine, benzoxazole or benzothiazole, an electrically conductive high-molecular weight oligomer such as a poly(N-vinylcarbazole) derivative, an aniline copolymer, a thiophene oligomer and a polythiophene, a high-molecular weight compound such as a polythiophene derivative, a polyphenylene derivative, a polyphenylenevinylene derivative and a polyfluorene derivative. The host compound may be used alone or in combination of two or more.

More specific examples are shown below.

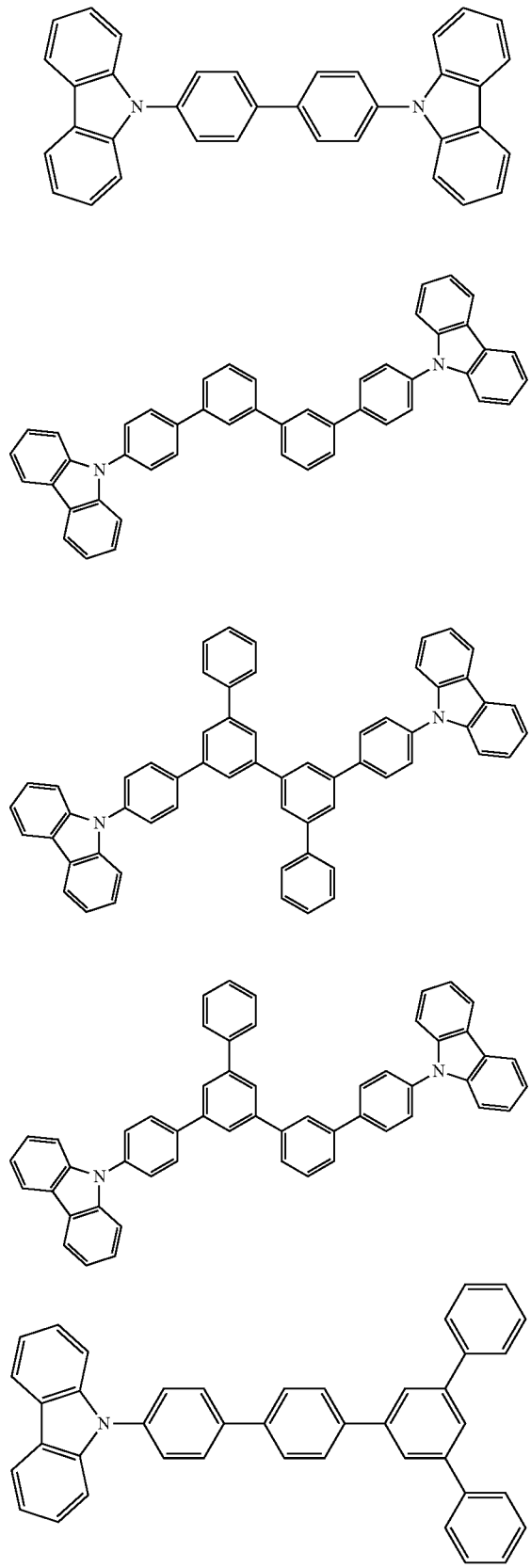

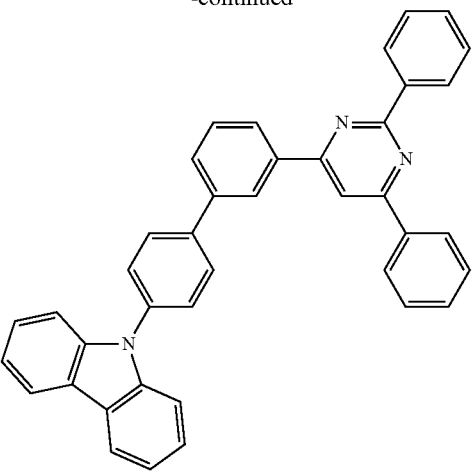

The phosphorescent dopant is a compound capable of emitting light from the triplet exciton. The phosphorescent dopant is not restricted as long as it emits light from the triplet exciton, and preferably a metal complex containing at least one metal selected from the group consisting of Ir, Ru, Pd, Pt, Os and Re, more preferably a porphyrin metal complex or an orthometalated metal complex. As the porphyrin metal complex, a porphyrin platinum complex is preferable. The phosphorescent compound may be used alone or in combination of two more.

Various ligands form the orthometalated metal complex, and preferred examples thereof include 2-phenylpyridine derivatives, 7,8-benzoquinoline derivatives, 2-(2-thienyl)pyridine derivatives, 2-(1-naphthyl)pyridine derivatives, and 2-phenylquinoline derivatives. These derivatives may be substituted, if necessary. In particular, a dopant introduced with fluorine atom or trifluoromethyl group is preferable as the blue-emitting dopant. In addition, a ligand other than the above ligands such as acetylacetonate and picric acid may be introduced as a co-ligand.

The amount of the phosphorescent dopant in the light emitting layer may be appropriately selected without particular limitation, for example, it may be 0.1 to 70% by mass, preferably 1 to 30% by mass. If being 0.1% by mass or more, the light emission is prevented from being excessively lowered and the effect of using it is sufficient. If being 70% by mass or less, the concentration quenching is prevented and consequently the device performance is prevented from being deteriorated.

The light emitting layer may contain a hole transporting material, an electron transporting material or a polymer binder, if necessary.

The thickness of the light emitting layer is preferably 5 to 50 nm, more preferably 7 to 50 nm, and most preferably 10 to 50 nm. If being 5 nm or more, the light emitting layer is easily formed and the control of color is easy. If being 50 nm or less, the driving voltage is prevented from increasing.

The light emitting layer may be included, if necessary, a known light emitting material other than the compound of the invention in an amount not adversely affecting the object of the invention. Alternatively, a light emitting layer containing a known light emitting material may be laminated on a light emitting layer containing the compound of the invention.

Hole Transporting Layer and Hole Injecting Layer

The hole transporting layer is a layer which facilitates the injection of holes into the light emitting layer and transports holes to the light emitting region. The layer has a large hole mobility and an ionization energy generally as small as 5.5 eV or lower. The hole transporting layer is preferably made from a material capable of transporting holes to the light emitting layer at a low electric field strength. The hole mobility of the hole transporting layer is preferably at least $10^{-4}$ cm$^2$/V·sec under an electric field of $10^4$ to $10^6$ V/cm.

Examples of the material for the hole transporting layer include triazole derivative, oxadiazole derivative, imidazole derivative, polyarylalkane derivative, pyrazoline derivative, pyrazolone derivative, phenylenediamine derivative, arylamine derivative, amino-substituted chalcone derivative, oxazole derivative, styrylanthracene derivative, fluorenone derivative, hydrazone derivative, stilbene derivative, silazane derivative, polysilane-based copolymer, aniline-based copolymer, and electrically conductive high-molecular oligomer (particularly, thiophene oligomer).

The hole injecting layer is used to facilitate the injection of holes. The material for organic EL devices of the invention may be used as the material for the hole injecting layer alone or in combination with another material, for example, the materials mentioned with respect to the hole transporting layer. In addition, a porphyrin compound, an aromatic tertiary amine compound, and a styryl amine compound are also usable.

Also usable are a compound having two fused aromatic rings, for example, 4,4'-bis(N-(1-naphthyl)-N-phenylamino) biphenyl (NPD), and a compound having three triphenylamine units connected in star burst configuration, for example, 4,4',4"-tris(N-(3-methylphenyl)-N-phenylamino) triphenylamine (MTDATA).

An aromatic dimethylidene compound, a inorganic compound of p-type Si, and an inorganic compound of p-type SiC are also usable as the material for the hole injecting layer.

The hole injecting layer and the hole transporting layer may be formed by making the compound mentioned above into a thin film by a known method, such as a vacuum vapor deposition method, a spin coating method, a casting method, and LB method. The thickness of the hole injecting layer and the hole transporting layer is generally 1 nm to 5 μm, although not particularly limited thereto.

The hole injecting, transporting layer may be a single layer made of one or more kinds of the materials mentioned above or may be laminated with a different hole injecting, transporting layer, as long as the hole injecting, transporting layer contains the compound of the present invention in the hole transporting region.

An organic semiconductor layer serves as a part of the hole transporting layer and assists the injection of holes or electrons into the light emitting layer. The electrical conductivity thereof is preferably $10^{-10}$ S/cm or more. Examples of the material for the organic semiconductor layer include an electrically conductive oligomer, such as an oligomer having thiophene and an oligomer having arylamine disclosed in JP 8-193191A, and an electrically conductive dendrimer, such as a dendrimer having an arylamine.

Electron Injecting/Transporting Layer

The electron injecting/transporting layer is a layer having a large electron mobility, which facilitates the injection of electrons into the light emitting layer and transports them to a light emitting region.

The film thickness of the electron transporting layer is selected from several meters to several micrometers. When the film thickness is large, the electron mobility is preferably at least $10^{-5}$ cm$^2$/V·s under an electric field of $10^4$ to $10^6$ V/cm to avoid the increase of driving voltage.

As the material for the electron injecting layer, metal complexes of 8-hydroxyquinoline or derivatives thereof and oxadiazole derivatives are preferable. Examples of the metal complexes of 8-hydroxyquinoline and derivatives thereof include metal chelate oxinoid compounds including chelates of oxine (in general, 8-quinolinol or 8-hydroxyquinoline), for example, tris(8-quinolinol)aluminum.

Examples of the oxadiazole derivatives include an electron transfer compound represented by the following formulae:

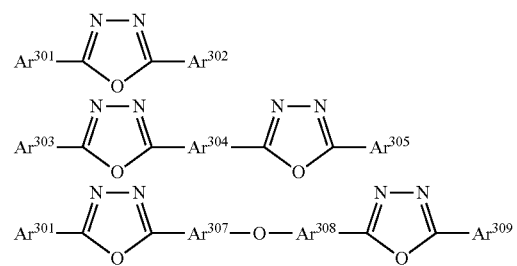

In the above formulae, $Ar^{301}$, $Ar^{302}$, $Ar^{303}$, $Ar^{305}$, $Ar^{306}$, and $Ar^{309}$ each independently represent a substituted or unsubstituted aryl group. $Ar^{304}$, $Ar^{307}$, and $Ar^{308}$ each independently represent a substituted or unsubstituted arylene group.

Examples of the aryl group include phenyl group, biphenyl group, anthranyl group, perilenyl group, and pyrenyl group. Examples of the arylene group include phenylene group, naphthylene group, biphenylene group, anthranylene group, perilenylene group, and pyrenylene group. Examples of the substituent include an alkyl group having 1 to 10 carbon atoms, an alkoxy group having 1 to 10 carbon atoms and cyano group. The electron transporting compound is preferably a thin-film forming compound.

Specific examples of the electron transporting compounds are:

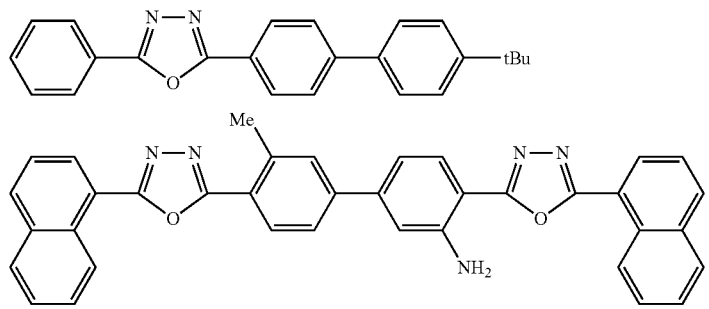

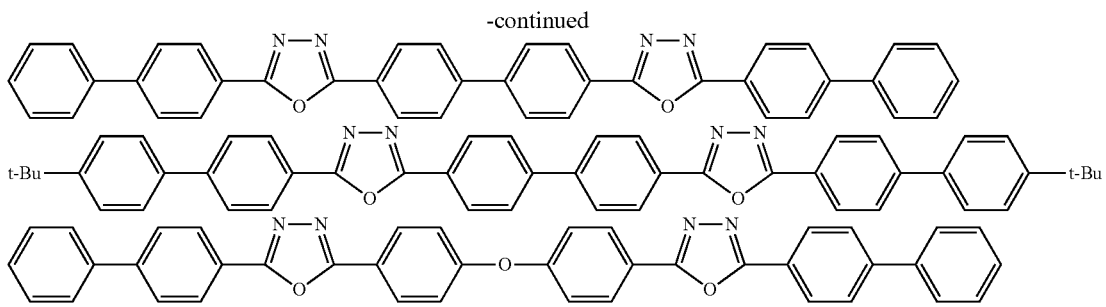

wherein Me is methyl group and t-Bu is t-butyl group.

The compounds represented by the following formulae (A) to (F) may be also used as the material for the electron injecting layer and the electron transporting layer.

A nitrogen-containing heteroring derivative represented by formula (A) or (B):

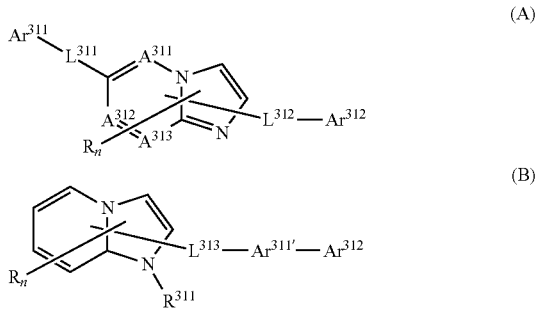

wherein $A^{311}$ to $A^{313}$ each independently represent a nitrogen atom or a carbon atom; $Ar^{311}$ represents a substituted or unsubstituted aryl group having 6 to 60 nuclear carbon atoms or a substituted or unsubstituted heteroaryl group having 3 to 60 nuclear carbon atoms; $Ar^{311'}$ represents a substituted or unsubstituted arylene group having 6 to 60 nuclear carbon atoms or a substituted or unsubstituted heteroarylene group having 3 to 60 nuclear atoms; $Ar^{312}$ represents a hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms, or a substituted or unsubstituted alkoxy group having 1 to 20 carbon atoms, with the proviso that at least one of $Ar^{311}$ and $Ar^{312}$ is a substituted or unsubstituted condensed ring group having 10 to 60 nuclear carbon atoms or a substituted or unsubstituted monohetero condensed ring group having 3 to 60 nuclear atoms.

$L^{311}$, $L^{312}$, and $L^{313}$ each independently represents a single bond, a substituted or unsubstituted arylene group having 6 to 60 nuclear carbon atoms, a substituted or unsubstituted heteroarylene group having 3 to 60 nuclear atoms, or a substituted or unsubstituted fluorenylene group.

R and $R^{311}$ each independently represent a hydrogen atom, a substituted or unsubstituted aryl group having 6 to 60 nuclear carbon atoms, a substituted or unsubstituted heteroaryl group having 3 to 60 nuclear atoms, a substituted or unsubstituted alkyl group having 1 to 20 carbon atoms, or a substituted or unsubstituted alkoxy group having 1 to 20 carbon atoms; n represents an integer of 0 to 5; when n is 2 or more, R groups may be the same or different and adjacent R groups may bond to each other to form an aliphatic ring or an aromatic ring.

A nitrogen-containing heteroring derivative represented by formula (C):

$$HAr-L^{314}-Ar^{321}-Ar^{322} \qquad (C)$$

wherein HAr represents a nitrogen-containing heterocyclic group having 3 to 40 carbon atoms which may be substituted; $L^{314}$ represents a single bond, an arylene group having 6 to 60 carbon atoms which may be substituted, a heteroarylene group having 3 to 60 carbon atoms which may be substituted or a fluorenylene group which may be substituted; $Ar^{321}$ represents a divalent aromatic hydrocarbon group having 6 to 60 carbon atoms which may be substituted; and $Ar^{322}$ represents an aryl group having 6 to 60 carbon atoms which may be substituted or a heteroaryl group having 3 to 60 carbon atoms which may be substituted.

A silacyclopentadiene derivative represented by formula (D):

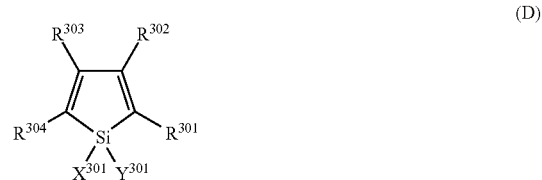

wherein $X^{301}$ and $Y^{301}$ each independently represent a saturated or unsaturated hydrocarbon group having 1 to 6 carbon atoms, an alkoxy group, an alkenyloxy group, an alkynyloxy group, a hydroxy group, a substituted or unsubstituted aryl group, or a substituted or unsubstituted heteroring, or $X^{301}$ and $Y^{301}$ represent a saturated or unsaturated ring by bonding to each other; $R^{301}$ to $R^{304}$ each independently represents a hydrogen atom, a halogen atom, a substituted or unsubstituted alkyl group, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heteroring group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group. These groups may be substituted and adjacent groups may form a substituted or unsubstituted condensed ring.

A borane derivative represented by formula (E):

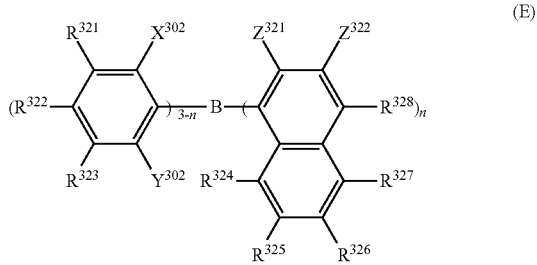

wherein $R^{321}$ to $R^{328}$ and $Z^{322}$ each independently represent a hydrogen atom, a saturated or unsaturated hydrocarbon group, an aromatic hydrocarbon group, a heteroring group, a substituted amino group, a substituted boryl group, an alkoxy group, or an aryloxy group; $X^{302}$, $Y^{302}$ and $Z^{321}$ each independently represent a saturated or unsaturated hydrocarbon group, an aromatic hydrocarbon group, a heteroring group, a substituted amino group, an alkoxy group, or an aryloxy group; $Z^{321}$ and $Z^{322}$ may bond to each other to form a condensed ring; n represents an integer of 1 to 3; and when n or (3−n) is 2 or more, $R^{321}$ groups to $R^{328}$ groups, $X^{302}$ groups, $Y^{302}$ groups, $Z^{322}$ groups, and $Z^{321}$ groups may be the same or different.

A gallium complex represented by formula (F):

wherein $Q^{301}$ and $Q^{302}$ each independently represent a ligand represented by the following formula (K), $L^{315}$ represents a halogen atom, a substituted or unsubstituted alkyl group, a substituted or unsubstituted cycloalkyl group, a substituted or unsubstituted aryl group, a substituted or unsubstituted heterocyclic group, —OR (wherein R represents a hydrogen atom, a substituted or unsubstituted alkyl group, a substituted or unsubstituted cycloalkyl group, a substituted or unsubstituted aryl group, or a substituted or unsubstituted heterocyclic group), or a ligand represented by —O—Ga-$Q^{303}(Q^{304})$ wherein $Q^{303}$ and $Q^{304}$ are as defined in $Q^{301}$ and $q^{302}$.

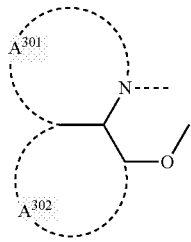

wherein rings $A^{301}$ and $A^{302}$ each represent a condensed six-membered aryl ring which may be substituted.

This metal complex strongly exhibits a character of n-type semiconductor and has a large electron injection ability. Since the energy of forming complex is small, the metal and the ligand in resulting metal complex bond strongly to each other, to increase the fluorescence quantum efficiency of light emitting material.

Specific examples of the substituents of rings $A^{301}$ and $A^{302}$ each forming the ligand represented by formula (K) include a halogen atom, such as chlorine, bromine, iodine, and fluorine; a substituted or unsubstituted alkyl group, such as methyl group, ethyl group, propyl group, butyl group, s-butyl group, t-butyl group, pentyl group, hexyl group, heptyl group, octyl group, stearyl group, and trichloromethyl group; a substituted or unsubstituted aryl group, such as phenyl group, naphthyl group, biphenyl group, anthranyl group, phenanthryl group, fluorenyl group, pyrenyl group, 3-methylphenyl group, 3-methoxyphenyl group, 3-fluorophenyl group, 3-trichloromethylphenyl group, 3-trifluoromethylphenyl group, and 3-nitrophenyl group; a substituted or unsubstituted alkoxyl group, such as methoxy group, n-butoxy group, t-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group; a substituted or unsubstituted aryloxy group, such as phenoxy group, p-nitrophenoxy group, p-t-butylphenoxy group, 3-fluorophenoxy group, pentafluorophenyl group, and 3-trifluoromethylphenoxy group; a substituted or unsubstituted alkylthio group, such as methylthio group, ethylthio group, t-butylthio group, hexylthio group, octylthio group, and trifluoromethylthio group; a substituted or unsubstituted arylthio group, such as phenylthio group, p-nitrophenylthio group, p-t-butylphenylthio group, 3-fluorophenylthio group, pentafluorophenylthio group, and 3-trifluoromethylphenylthio group; cyano group; nitro group; amino group; a mono- or di-substituted amino group, such as methylamino group, diethylamino group, ethylamino group, diethylamino group, dipropylamino group, dibutyl amino group, and diphenylamino group; an acylamino group, such as bis(acetoxymethyl) amino group, bis(acetoxyethyl)amino group, bis(acetoxypropyl)amino group, and bis(acetoxybutyl)amino group; hydroxyl group; siloxy group; acyl group; a substituted or unsubstituted carbamoyl group, such as carbamoyl group, methylcarbamoyl group, dimethylcarbamoyl group, ethylcarbamoyl group, diethylcarbamoyl group, propylcarbamoyl group, butylcarbamoyl group, and phenylcarbamoyl group; carboxyl group; sulfonic acid group; imido group; a cycloalkyl group, such as cyclopentyl group and cyclohexyl group; and a heterocyclic group, such as pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, and benzimidazolyl group. The above substituents may bond to each other to form a six-membered aryl ring or heteroring.

In a preferred embodiment of the organic EL device, a reductive dopant is included in an electron transporting region or an interfacial region between a cathode and an organic layer. The reductive dopant is defined as a substance capable of reducing an electron transporting compound. Therefore, various compounds having a certain level of reducing property may be used as the reductive dopant. Examples thereof include at least one compound selected from alkali metals, alkaline earth metals, rare earth metals, alkali metal oxides, alkali metal halides, alkaline earth metal oxides, alkaline earth metal halides, rare earth metal oxides, rare earth metal halides, alkali metal carbonates, alkaline earth metal carbonates, rare earth metal carbonates, organic complexes of alkali metals, organic complexes of alkaline earth metals, and organic complexes of rare earth metals.

Examples of the preferred reductive dopant include at least one alkali metal selected from the group consisting of Li (work function: 2.9 eV), Na (work function: 2.36 eV), K (work function: 2.28 eV), Rb (work function: 2.16 eV), and Cs (work function: 1.95 eV) or at least one alkaline earth metal selected from the group consisting of Ca (work function: 2.9 eV), Sr (work function: 2.0 to 2.5 eV) and Ba (work function: 2.52 eV). A reductive dopant having a work function of 2.9 eV or less is particularly preferred.

Of the above, at least one alkali metal selected from the group consisting of K, Rb and Cs is more preferred, with Rb and Cs being still more preferred and Cs being most preferred.

Since these alkali metals have a particularly high reducing ability, the luminance and lifetime of the organic EL device are improved by the addition thereof into an electron injection region in a relatively small amount. A combination of two or more alkali metals is also preferably used as the reductive dopant having a work function of 2.9 eV or smaller. A combination containing Cs, for example, Cs and Na, Cs and K, Cs and Rb, and Cs, Na and K, is particularly preferred. By combinedly containing Cs, the reductive dopant exhibits an effective reducing ability and the luminance and lifetime of the organic EL device are improved by the addition thereof into the electron injection region.

In the organic EL device of the present invention, an electron injecting layer made of an insulating material or a semiconductor may be further disposed between the cathode and the organic layer. The electron injecting layer effectively prevents a leak of electric current, to improve the electron injection property.

The insulating material is preferably at least one metal compound selected from the group consisting of alkali metal chalcogenide, alkaline earth metal chalcogenide, alkali metal halide, and alkaline earth metal halide. When the electron injecting layer is made of these alkali metal chalcogenides, the electron injection property is further improved.

Specific examples of preferred alkali metal chalcogenide include $Li_2O$, LiO, $Na_2S$, $Na_2Se$, and NaO. Specific examples of preferred alkaline earth metal chalcogenide include CaO, BaO, SrO, BeO, BaS, and CaSe. Specific examples of preferred alkali metal halide include LiF, NaF, KF, CsF, LiCl, KCl, and NaCl. Specific examples of preferred alkaline earth metal halide include fluorides, such as $CaF_2$, $BaF_2$, $SrF_2$, $MgF_2$, and $BeF_2$, and halides other than fluorides.

Examples of the semiconductor for forming the electron transporting layer include oxides, nitrides and oxynitrides, alone or in combination of two or more, each containing at least one element selected from Ba, Ca, Sr, Yb, Al, Ga, In, Li, Na, Cd, Mg, Si, Ta, Sb, and Zn.

The electron transporting layer is preferably a crystallitic or amorphous, insulating thin film of an inorganic compound. Since the electron transporting layer is made more uniform by forming it from such an insulating thin film, the pixel defects, such as dark spots, can be decreased.

Examples of the inorganic compound include the alkali metal chalcogenides, the alkaline earth metal chalcogenides, the alkali metal halides and the alkaline earth metal halides which are described above.

Cathode

The cathode is formed from an electrode material, such as metal, alloy, electrically conductive compound and a mixture thereof, each having a small work function (4 eV or smaller). Examples of the electrode material include sodium, sodium-potassium alloy, magnesium, lithium, magnesium-silver alloy, aluminum/aluminum oxide, aluminum-lithium alloy, indium, and rare earth metal.

The cathode is formed by making the electrode material described above into a thin film by a process, such as a vapor deposition process and a sputtering process.

When the light emitted from the light emitting layer is taken out of the cathode, the transmittance of the cathode to the emitted light is preferably 10% or more. The sheet resistivity of the cathode is preferably several hundreds $\Omega/\square$ or less and the thickness of the cathode is generally 10 nm to 1 μm and preferably from 50 to 200 nm.

Insulating Layer

Since the ultra-thin films of organic EL devices are affected by the action of electric field, the pixel defects due to leak and short circuit tends to occur. To prevent the defects, an insulating thin film layer (insulating layer) is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

Production of Organic EL Device

The organic EL device is produced, for example, by forming an anode, a hole injecting layer, a hole transporting layer, a light emitting layer, an electron injecting layer, and other layers, and then forming a cathode, using the materials mentioned above. Alternatively, the organic EL device is produced by forming each layer in a reverse order from the cathode to the anode.

Example of the production of an organic EL device having a layered structure of anode/hole injecting layer/hole transporting layer/light emitting layer/electron transporting layer/cathode on a light-transmissive substrate will be described below.

First, on a suitable light-transmissive substrate, an anode is formed by making the anode material into a thin film having a thickness of 1 μm or less, preferably 10 to 200 nm by a method, such as vapor deposition and sputtering.

Then, a hole injecting layer and a hole transporting layer are formed on the anode. These layers may be formed by a vacuum vapor deposition method, a spin coating method, a casting method or LB method, with the vacuum vapor deposition method being preferred because a uniform film is easily obtained and pinholes are hardly formed.

The conditions of the vacuum vapor deposition method for forming the hole injecting layer and the hole transporting layer depend upon the crystalline structure, the recombination structure, and other factors of the intended hole injecting layer and hole transporting layer, and the vacuum vapor deposition is conducted preferably under the conditions: a deposition source temperature of 50 to 450° C., a vacuum degree of 10 to $10^{-3}$ torr, a deposition speed of 0.01 to 50 nm/s, a substrate temperature of −50 to 300° C., and a film thickness of 1 nm to 5 μm.

Then, a light emitting layer is formed on the hole transporting layer. The light emitting layer is formed by making an organic light emitting material into a thin film by a vacuum vapor deposition method, a spin coating method, or a casting method, with the vacuum vapor deposition method being preferred because a uniform film is easily obtained and pinholes are hardly formed. The conditions of the vacuum vapor deposition method for forming the light emitting layer depend upon the kind of the compound to be used, and generally selected from those mentioned with respect to the hole transporting layer.

Next, an electron transporting layer is formed on the light emitting layer. Like the formation of the hole transporting layer and the light emitting layer, the electron transporting layer is formed preferably by the vacuum vapor deposition method because a uniform thin film is needed. The conditions of the vacuum vapor deposition are selected from those mentioned with respect to the hole transporting layer and the light emitting layer.

Finally, a cathode is formed on the electron injecting layer, to obtain an organic EL device.

The cathode is made of a metal and can be formed by the vapor deposition method or the sputtering method, with the vacuum vapor deposition method being preferred in view of preventing the underlying organic layers from being damaged during the film forming process.

In the production of organic EL device mentioned above, the layers from the anode to the cathode are successively formed preferably in a single evacuation operation.

The organic EL device emits light when a voltage is applied between the electrodes, for example, when a direct voltage of 5 to 40 V is applied with the anode being + terminal and the cathode being − terminal. If a voltage is applied in the reverse polarity, no electric current flows and light is not emitted. When an alternating voltage is applied, the uniform light emission is observed only in the polarity where the anode is + and the cathode is −. The wave shape of alternating voltage in not limited.

EXAMPLES

The present invention will be described in more detail with reference to the examples. However, it should be noted that the scope of the invention is not limited thereto.

The compounds synthesized or used in the following examples are shown below.

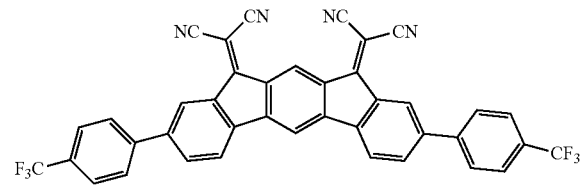
(A-1)

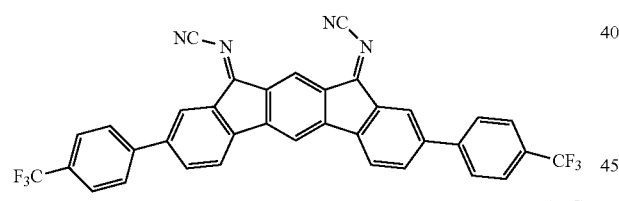
(A-2)

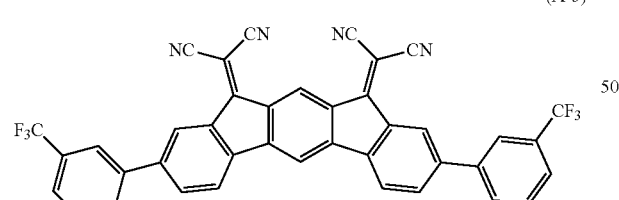
(A-5)

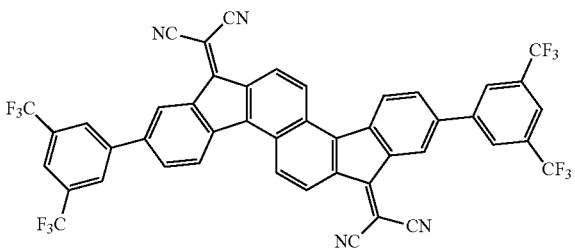
(A-49)

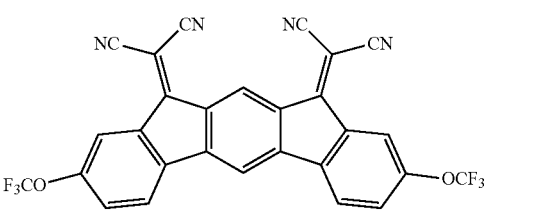
(A-55)

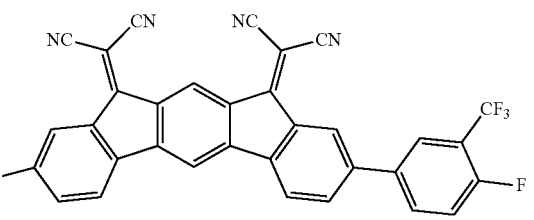
(A-64)

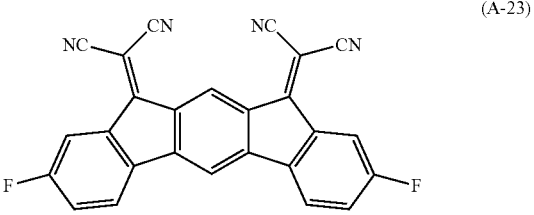
(A-23)

Example 1

Synthesis of Indenofluorenedione Derivative (A-1)

(1) Synthesis of Intermediate A

Intermediate A was synthesized according to the following synthesis scheme:

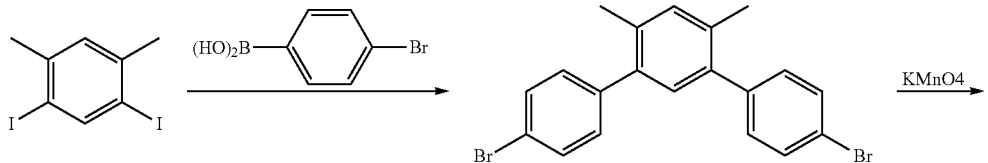

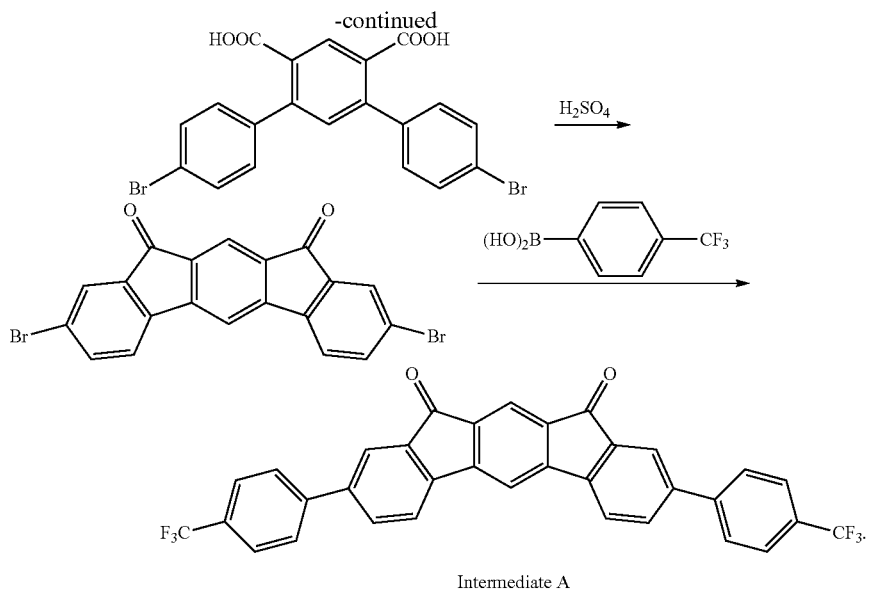

Intermediate A

A mixture of 5.0 g of 1,5-diiodo-2,4-dimethylbenzene, 5.8 g of 4-bromophenylboronic acid, 0.65 g of tetrakis(triphenylphosphine)palladium(0), 44 ml of 2 M sodium carbonate, and 40 ml of toluene was refluxed under stirring in argon stream for 8 h. After cooling, the reaction product solution was filtered, washed with water and then methanol, and purified on a silica gel column (developer: methylene chloride), to obtain 4.5 g of white solids. Mass spectrometric measurement of the obtained white solids showed a peak at M/Z=416.

Next, a mixture of 4.5 g of the white solids obtained above, 13.0 g of potassium permanganate, 15 ml of pyridine, and 25 ml of water was heated under stirring at 100° C. for 8 h. After removing the solid matter by hot filtration, the filtrate was neutralized by adding a 1 N hydrochloric acid dropwise. The precipitated white solids separated by filtration was washed with a diluted hydrochloric acid and then ion exchanged water and dried, to obtain 2.7 g of white solids.

The white solids were added to 20 ml of concentrated sulfuric acid, and the resultant mixture was heated under stirring at 70° C. for 12 h. The reaction product solution was allowed to cool and poured into iced water. The orange solids were collected by filtration, washed with ion exchanged water, and dried to obtain 2.3 g of solids. Mass spectrometric measurement of the obtained solids showed a peak at M/Z=440.

A mixture of 2.3 g of the obtained dibrominated compound, 3.0 g of 4-trifluoromethylphenylboronic acid, 0.24 g of tetrakis(triphenylphosphine)palladium(0), 25 ml of 2 M sodium carbonate and 110 ml of toluene was refluxed under stirring in argon stream for 8 h. After cooling, the reaction product solution was filtered and washed with water, methanol, and then toluene, to obtain 2.1 g of orange solids (intermediate A).

A mass spectrometric measurement of the obtained solids showed a peak at M/Z=570.

(2) Synthesis of Compound (A-1)

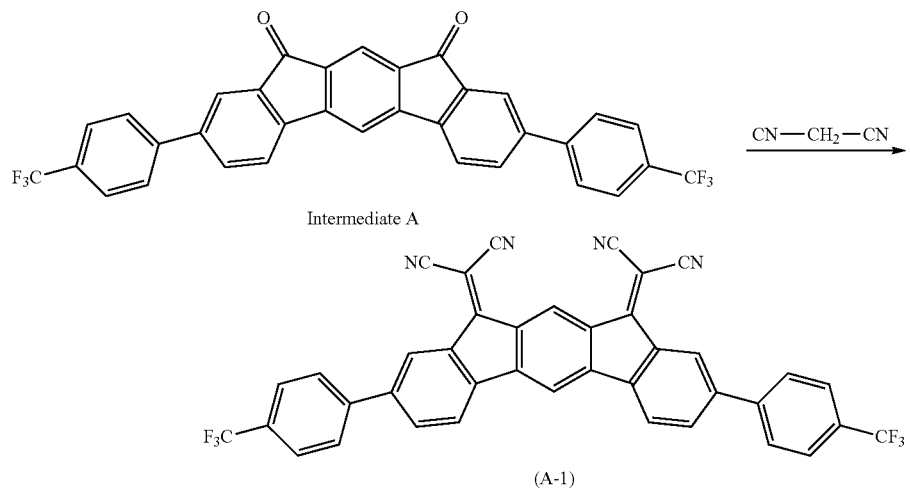

A mixture of 1.5 g of the intermediate A, 0.41 g of malononitrile, and 50 ml of pyridine was heated under stirring at 80° C. for 8 h. After allowing the mixture to cool, the precipitated solids were collected by filtration, washed with water, methanol, and then toluene, and vacuum-dried. The dried solids were purified by sublimation at 350° C., to obtain 1.5 g of purple crystals. Through IR measurement of the obtained compound, it was found that the absorption at 1730 cm$^{-1}$ attributable to carbonyl group disappeared and the absorption attributable to cyano group appeared at 2222 cm$^{-1}$. Mass spectrometric measurement showed a peak at M/Z=666.

The obtained compound was measured for the reduction potential in acetonitrile by cyclic voltammetry using tetrabutylammonium perchlorate (TBAP) as a supporting electrolyte and a silver-silver chloride electrode as a reference electrode. The reduction potential of compound (A-1) was −0.4 V at a sweeping speed of 0.1 V/s.

The first oxidation potential of ferrocene (Fc) used as the standard was 0.5 V when measured in the same manner as above. The reduction potential of the compound (A-1) on the basis of the oxidation potential of ferrocene (Fc) was −0.8 V (vs Fc$^+$/Fc).

Example 2

Synthesis of Indenofluorenedione Derivative (A-2)

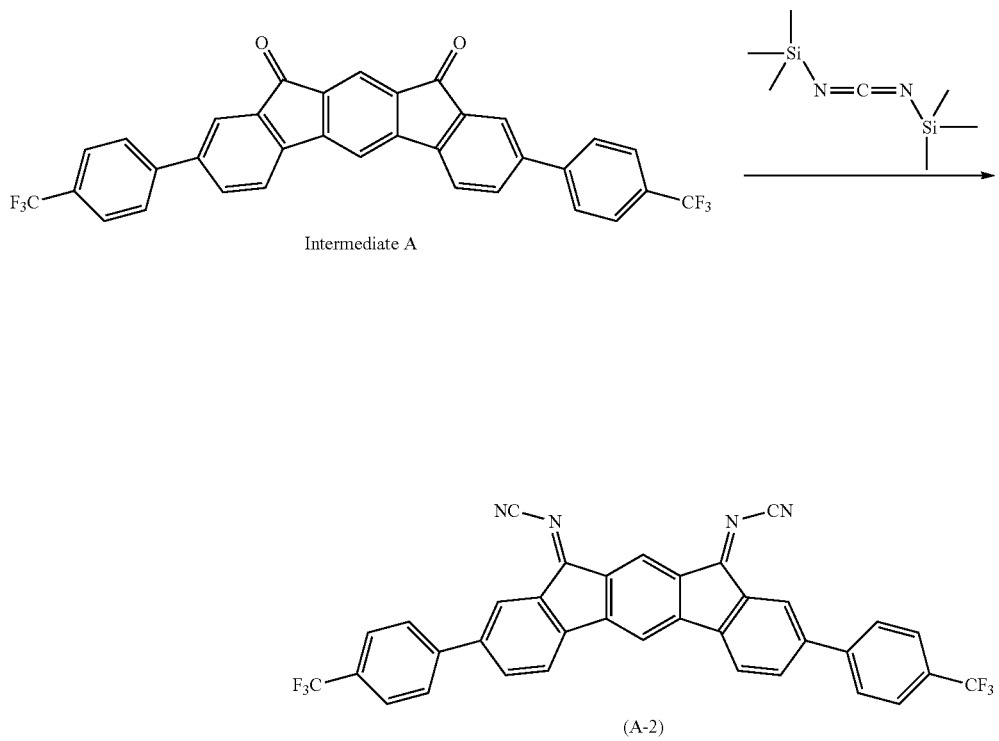

In a flask, 2.0 g of the intermediate A synthesized in Example 1 was dissolved in 100 ml of methylene chloride under stirring. After replacing the inside of the flask with argon, the solution was cooled to −10° C. on a sodium chloride/ice cooling bath. To the solution, 2.7 g of titanium tetrachloride was added and then a mixed liquid of 8.2 g of bist-rimethylsilylcarbodiimide and 40 ml of methylene chloride was added dropwise. After the dropwise addition, the solution was continuously cooled for 1 h, stirred for 4 h at room temperature, and then refluxed under stirring for 2 h. The precipitated reddish purple solids were collected by filtration and washed with methanol.

Through sublimation at 320° C., 1.2 g of the compound of the invention was obtained. Through IR measurement of the obtained compound, it was found that the absorption attributable to carbonyl group disappeared and the absorption attributable to cyano group appeared at 2180 cm$^{-1}$. Mass spectrometric measurement showed a peak at M/Z=618.

The obtained compound was measured for the reduction potential by cyclic voltammetry in the same manner as in Example 1. The reduction potential of the compound (A-2) on the basis of the first oxidation potential of the standard ferrocene (Fc) was −0.95 V (vs Fc$^+$/Fc).

Example 3

Synthesis of Indenofluorenedione Derivative (A-5)

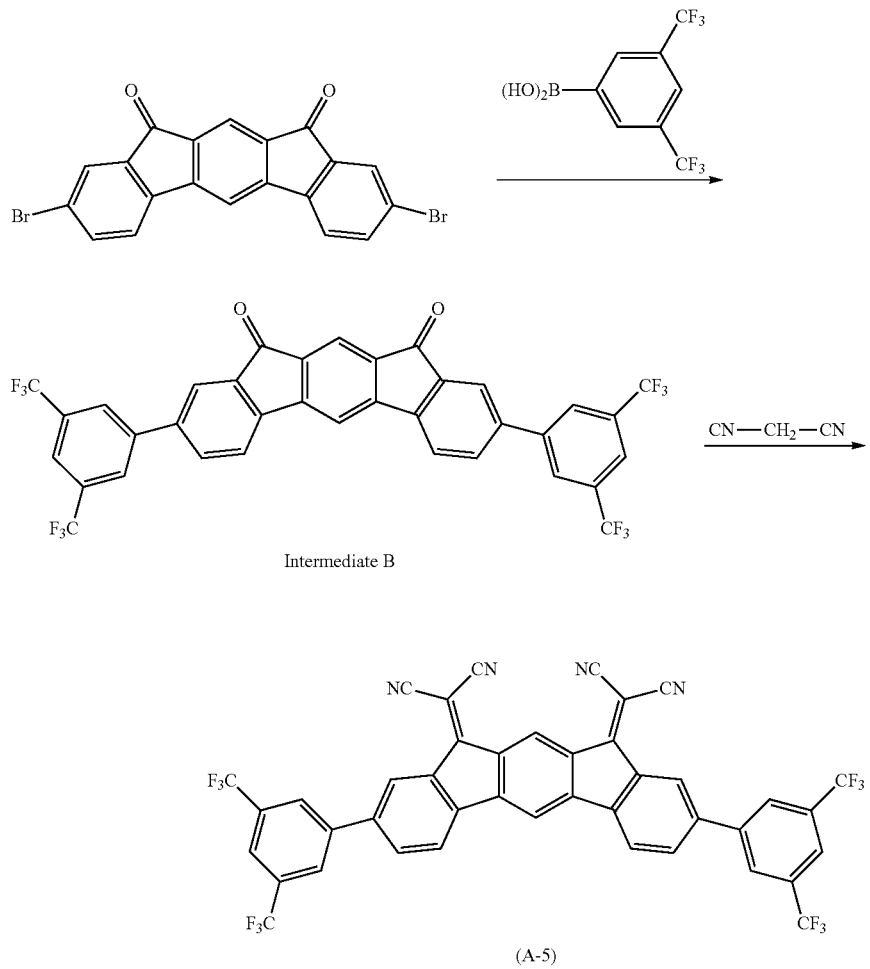

(A-5)

(1) Synthesis of Intermediate B

In the same manner as in the synthesis of intermediate A in Example 1 except for using 4.0 g of 3,5-bistrifluoromethylphenylboronic acid in place of 3.0 g of 4-trifluoromethylphenylboronic acid, 2.9 g of the intermediate B was obtained. The mass spectrometric measurement of the obtained solids showed a peak at M/Z=706.

(2) Synthesis of Indenofluorenedione Derivative (A-5)

In the same manner as in the synthesis of compound (A-1) in Example 1 except for changing 1.5 g intermediate A to 1.8 g of intermediate B, solids were obtained, which were purified by sublimation at 340° C., to obtain 1.5 g of dark purple crystals.

Through IR measurement of the obtained compound, it was found that the absorption attributable to carbonyl group disappeared and the absorption attributable to cyano group appeared at 2220 cm$^{-1}$. Mass spectrometric measurement showed a peak at M/Z=802.

The reduction potential of the obtained compound was measured by cyclic voltammetry in the same manner as in Example 1. The reduction potential of the compound (A-5) on the basis of the first oxidation potential of the standard ferrocene (Fc) was −0.88 V (vs Fc+/Fc).

Example 4

Synthesis of Indenofluorenedione Derivative (A-49)

(1) Synthesis of Intermediate C

Intermediate C was synthesized according to the following scheme.

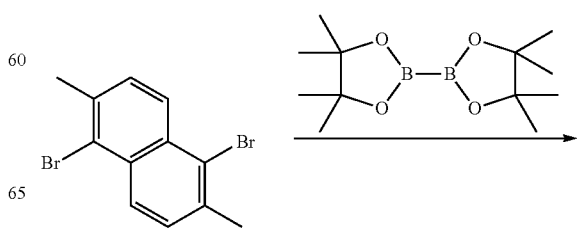

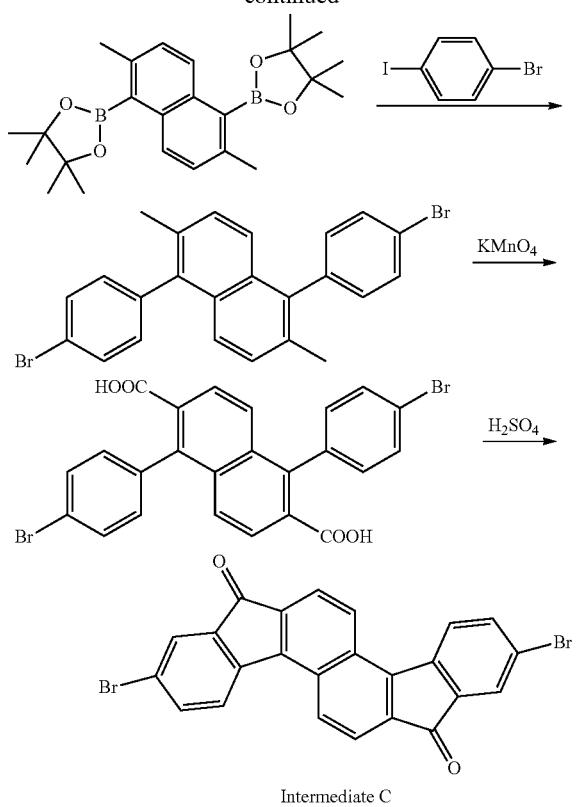

Intermediate C

In argon atmosphere, 17 g of 1,5-dibromo-2,7-dimethyl-naphthalene, 35 g of bispinacolate diboron, 2.8 g of Pd(dppf)Cl$_2$, 22 g of potassium acetate, and 400 ml of DMF were charged into a flask. The mixture was heated under stirring at 80° C. for 65 h. After cooling, the precipitate was collected by filtration, washed with water and then toluene, and dried.

Then, a mixture of 15 g of the obtained boronic ester, 27 g of bromoiodobenzene, 1.9 g of tetrakis(triphenylphosphine), 26 g of sodium carbonate, 120 ml of water, and 420 ml of DME in a flask was heated under stirring in argon atmosphere at 78° C. for 665 h. After cooling, the precipitate was collected by filtration, washed with water and then methanol, and recrystallized from toluene.

Then, a mixture of 13 g of the obtained dibrominated compound and 120 ml of pyridine in a flask was heated to 95° C. Thereafter, 10 g of potassium permanganate and 10 ml of ion exchanged water were added to the mixture. Then, 13 portions of 2 g of potassium permanganate and 2 ml of water were added to the mixture every ten minutes. The reaction product solution was hot-filtered and the filtrate was neutralized by a 2 N hydrochloric acid. The precipitated white solids were collected by filtration and washed with water.

Finally, a mixture of 15 g of the obtained dicarboxylic compound and 300 ml of a concentrated sulfuric acid in a flask was heated under stirring at 85° C. for 3 h. After cooling, the reaction product solution was slowly added to iced water, and the precipitated solids were collected by filtration and washed with ion exchanged water. The solids were further purified by sublimation, to obtain 7 g of the intermediate C. Through IR measurement of the obtained compound, it was found that the absorption attributable to carbonyl group appeared at 1720 cm$^{-1}$. Mass spectrometric measurement showed a peak at M/Z=802.

(2) Synthesis of Intermediate D

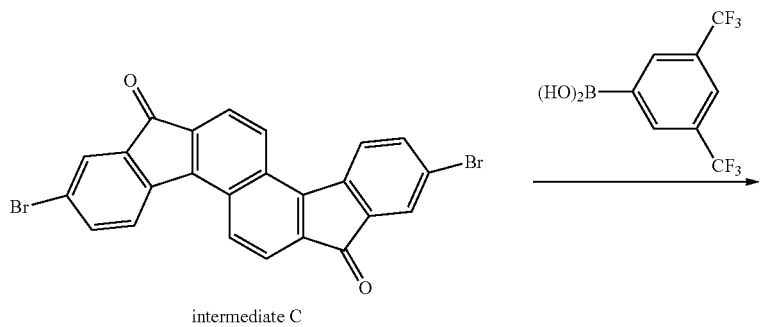

intermediate C

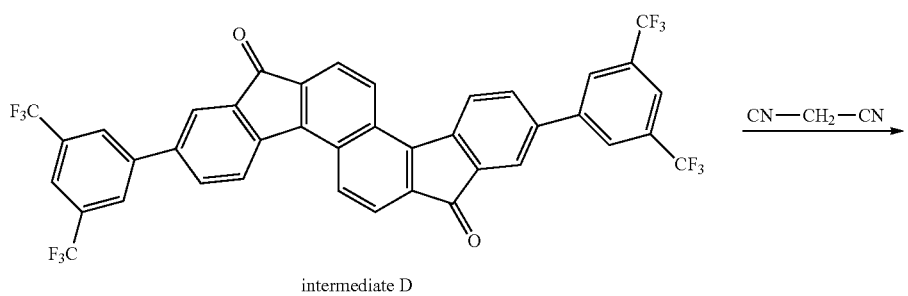

intermediate D

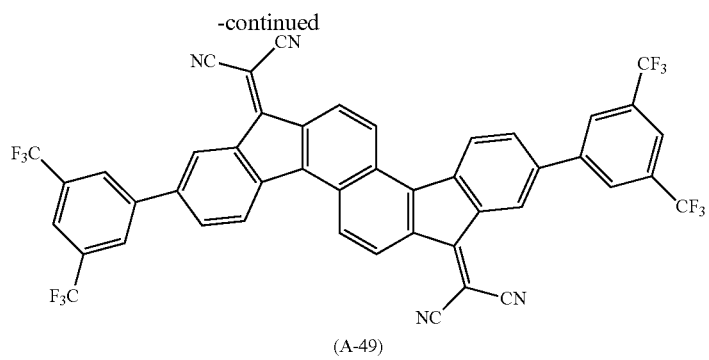

(A-49)

A mixture of 2.7 g of the intermediate C, 4.4 g of 3,5-bis(trifluoromethyl)phenylboronic acid, 0.26 g of tetrakis(triphenylphosphine)palladium(0), 25 ml of 2 M sodium carbonate, and 110 ml of toluene was refluxed under stirring in argon stream for 8 h. After cooling, the reaction product solution was filtered to collect the solids which were then washed with water, methanol, and then toluene, to obtain 3.0 g of orange solids (intermediate D).

Mass spectrometric measurement on the obtained solids showed a peak at M/Z=756.

(3) Synthesis of Compound (A-49)

A mixture of 1.4 g of the intermediate D synthesized above, 0.5 g of malononitrile, and 55 ml of pyridine was heated under stirring at 110° C. for 8 h. After allowing the mixture to cool, the solids were collected by filtration, washed with water, methanol, and then toluene, and vacuum-dried. The solids were then purified by sublimation at 360° C., to obtain 1.3 g of dark purple crystals. Through IR measurement of the obtained compound, it was found that the absorption at 1720 $cm^{-1}$ attributable to carbonyl group disappeared and the absorption attributable to cyano group appeared at 2220 $cm^{-1}$. Mass spectrometric measurement showed a peak at M/Z=852.

The obtained compound was measured for the reduction potential by cyclic voltammetry in the same manner as in Example 1. The reduction potential of the compound (A-49) on the basis of the first oxidation potential of the standard ferrocene (Fc) was −0.65 V (vs $Fc^+/Fc$).

Example 5

Synthesis of Indenofluorenedione Derivative (A-55)

The synthesis was conducted according to the following scheme.

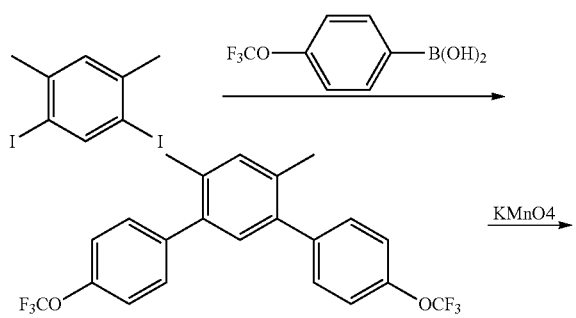

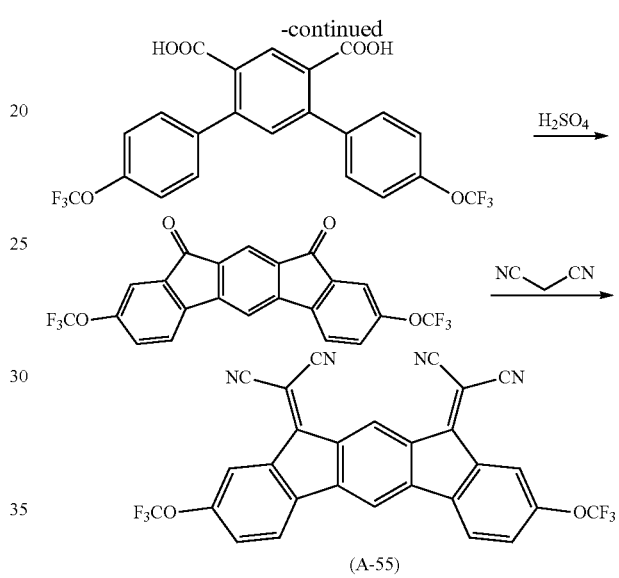

(A-55)

A mixture of 3.0 g of 1,5-diiodo-2,4-dimethylbenzene, 3.6 g of 4-trifluoromethoxyphenylboronic acid, 0.39 g of tetrakis(triphenylphosphine)palladium(0), 26 ml of 2 M sodium carbonate, and 21 ml of toluene was refluxed under stirring in argon stream for 8 h. After cooling, the reaction product solution was filtered, washed with water and then methanol, and purified on a silica gel column (developer: methylene chloride), to obtain 3.7 g of white solids. Mass spectrometric measurement on the obtained white solids showed a peak at M/Z=426.

Then, a mixture of 3.5 g of the white solids, 2.0 g of potassium permanganate, 13 ml of pyridine, and 25 ml of water was heated under stirring at 100° C. Thereafter, 1.5-g portions of potassium permanganate were added to the mixture every 30 min in total amount of 18 g. After heating under stirring for 8 h from starting the reaction, the solid matter was removed from the mixture by hot filtration. The filtrate was neutralized by adding a 1 N hydrochloric acid dropwise. The precipitated white solids were collected by filtration, washed with a diluted hydrochloric acid and then ion exchanged water, and dried, to obtain 3.7 g of white solids.

Then, a mixture of the white solids and 20 ml of a concentrated sulfuric acid was heated under stirring at 50° C. for 12 h. The reaction product solution was allowed to stand for cooling and poured into iced water. The orange solids were collected by filtration, washed with ion exchanged water, and dried, to obtain 3.1 g of solids. Mass spectrometric measurement on the obtained solids showed a peak at M/Z=450.

Finally, a mixture of 1.7 g of the diquinone compound thus synthesized, 1.25 g of malononitrile, and 76 ml of pyridine was heated under stirring at 50° C. for 8 h. After allowing the mixture to cool, the solids were collected by filtration, washed with water, methanol, and then toluene, and vacuum-dried. Then the solids were purified by sublimation at 280° C., to obtain 1.5 g of purple crystals. Through IR measurement of the obtained compound, it was found that the absorption at 1730 cm$^{-1}$ attributable to carbonyl group disappeared and the absorption attributable to cyano group appeared at 2222 cm$^{-1}$. Mass spectrometric measurement showed a peak at M/Z=546.

The obtained compound was measured for the reduction potential by cyclic voltammetry in the same manner as in Example 1. The reduction potential of the compound (A-55) on the basis of the first oxidation potential of the standard ferrocene (Fc) was −0.88 V (vs Fc$^+$/Fc).

Example 6

Synthesis of Indenofluorenedione Derivative (A-64)

The synthesis was conducted according to the following scheme.

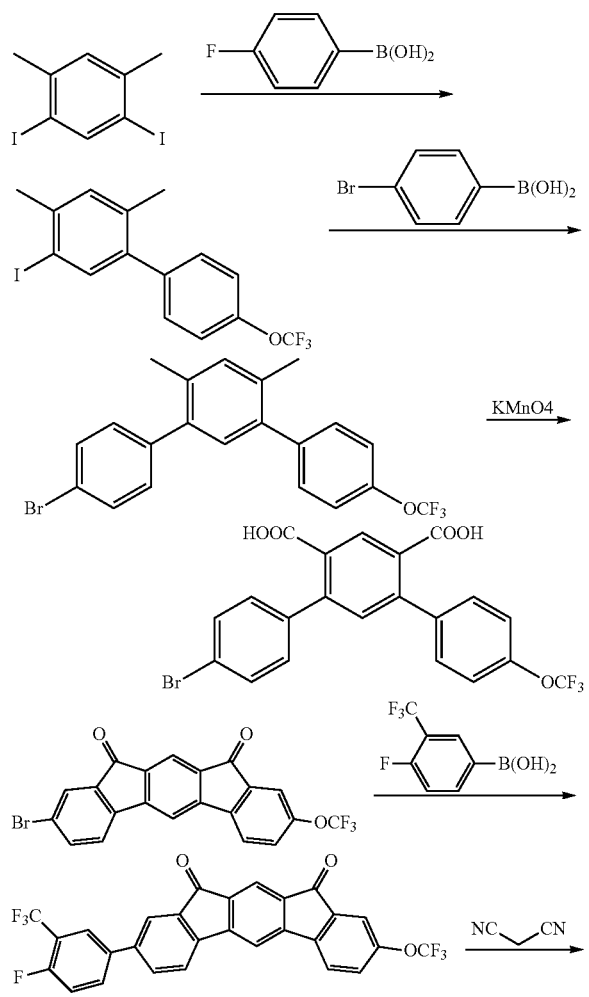

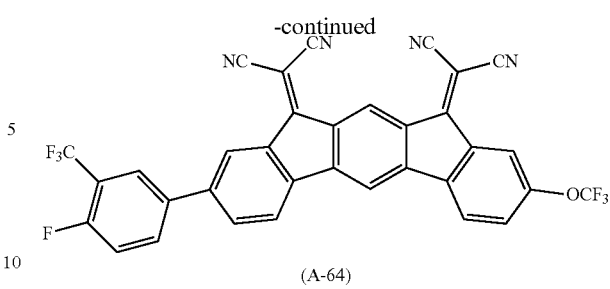

(A-64)

A mixture of 10 g of 1,5-diiodo-2,4-dimethylbenzene, 5.7 g of 4-trifluoromethoxyphenylboronic acid, 1.29 g of tetrakis (triphenylphosphine)palladium(0), 43 ml of 2 M sodium carbonate, and 70 ml of toluene was refluxed under stirring in argon stream for 6 h. After cooling, the reaction product solution was filtered, washed with water and then methanol, and purified on a silica gel column (developer: hexane), to obtain 3.0 g of white solids. Mass spectrometric measurement on the obtained white solids showed a peak at M/Z=392.

Next, a mixture of 2.9 g of the white solids, 1.8 g of 4-bromophenylboronic acid, 0.35 g of tetrakis(triphenylphosphine)palladium(0), 17 ml of 2 M sodium carbonate, and 19 ml of toluene was refluxed under stirring in argon stream for 6 h. After cooling, the reaction product solution was filtered, washed with water and then methanol, and purified on a silica gel column (developer: hexane), to obtain 1.6 g of white solids. Mass spectrometric measurement on the obtained white solids showed a peak at M/Z=421.

Next, a mixture of 1.6 g of white solids, 1.0 g of potassium permanganate, 6 ml of pyridine, and 10 ml of water was heated under stirring at 100° C. Thereafter, 1.5-g portions of potassium permanganate were added to the mixture every 30 min in a total amount of 13 g. After heating under stirring for 8 h from starting the reaction, the solid matter was removed by hot filtration and the filtrate was neutralized by adding a 1 N hydrochloric acid dropwise. The precipitated white solids collected by filtration was washed with a diluted hydrochloric acid and then ion exchanged water and dried, to obtain 1.5 g of white solids.

Then, a mixture of the white solids and 20 ml of a concentrated sulfuric acid was heated under stirring at 50° C. for 12 h. The reaction product solution was allowed to cool and then poured into iced water. The orange solids were collected by filtration, washed with ion exchanged water, and dried, to obtain 0.9 g of solids. Mass spectrometric measurement on the obtained solids showed a peak at M/Z=445.

A mixture of 0.8 g of the diquinone compound thus obtained, 0.5 g of 4-fluoro-3-trifluoromethylphenylboronic acid, 0.08 g of tetrakis(triphenylphosphine)palladium(0), 3 ml of 2 M sodium carbonate, and 4 ml of toluene was refluxed under stirring in argon stream for 8 h. After cooling, the reaction product solution was filtered to collect the solids which were washed with water, methanol, and then toluene, to obtain 0.7 g of range solids (intermediate A). Mass spectrometric measurement on the obtained solids showed a peak at M/Z=528.

Finally, a mixture of 0.7 g of the diquinone compound thus synthesized, 0.5 g of malononitrile, and 30 ml of pyridine was heated under stirring at 50° C. for 8 h. After allowing the mixture to cool, the solids were collected by filtration, washed with water, methanol, and then toluene, and vacuum-dried. The solids were then purified by sublimation at 320° C., to obtain 1.5 g of purple crystals. Through IR measurement of the obtained compound, it was found that the absorption at 1725 cm$^{-1}$ attributable to carbonyl group disappeared and the absorption attributable to cyano group appeared at 2220 cm$^{-1}$. Mass spectrometric measurement showed a peak at M/Z=624.

The obtained compound was measured for the reduction potential by cyclic voltammetry in the same manner as in Example 1. The reduction potential of the compound (A-3) on the basis of the first oxidation potential of the standard ferrocene (Fc) was −0.85 V (vs Fc$^+$/Fc).

Example 7

Synthesis of Indenofluorenedione Derivative (A-23)

The synthesis was conducted according to the following scheme.

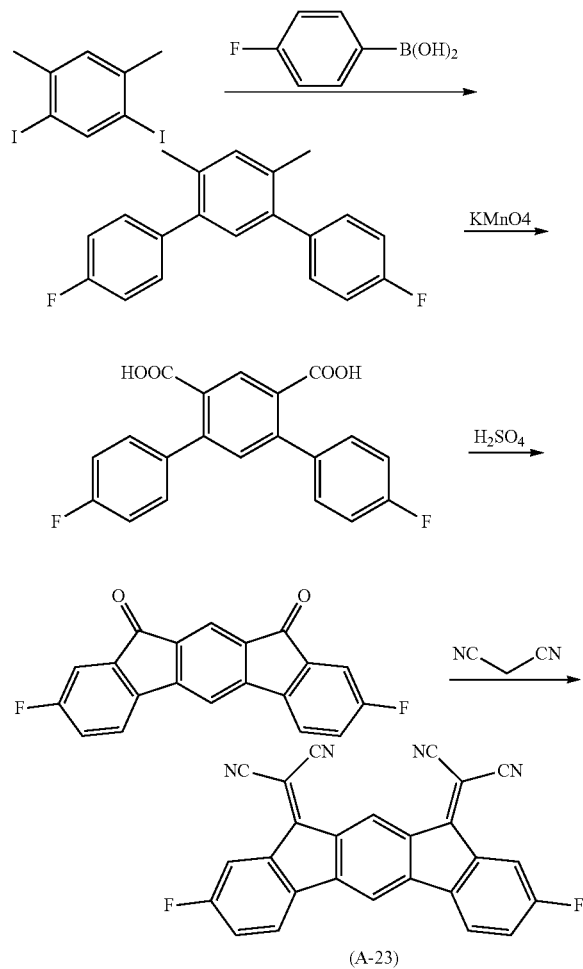

(A-23)

A mixture of 5.0 g of 1,5-diiodo-2,4-dimethylbenzene, 4.1 g of 4-fluorophenylboronic acid, 0.65 g of tetrakis(triphenylphosphine)palladium(0), 44 ml of 2 M sodium carbonate, and 40 ml of toluene was refluxed under stirring in argon stream for 8 h. After cooling, the reaction product solution was filtered, washed with water and then methanol, and purified on a silica gel column (developer: methylene chloride), to obtain 4.0 g of white solids. Mass spectrometric measurement on the obtained white solids showed a peak at M/Z=294.

Next, a mixture of 3.4 g of the white solids, 2.0 g of potassium permanganate, 13 ml of pyridine, and 25 ml of water was heated under stirring at 100° C. Thereafter, 1.5-g portions of potassium permanganate were added to the mixture every 30 min in a total amount of 18 g. After heating under stirring for 8 h from starting the reaction, the solid matter was removed by hot filtration and the filtrate was neutralized by adding a 1 N hydrochloric acid dropwise. The precipitated white solids collected by filtration were washed with a diluted hydrochloric acid and then ion exchanged water and dried, to obtain 3.1 g of white solids.

Then, a mixture of the white solids and 30 ml of a concentrated sulfuric acid was heated under stirring at 50° C. for 12 h. The reaction product solution was allowed to cool and poured into iced water. The orange solids were collected by filtration, washed with ion exchanged water, and dried, to obtain 2.8 g of solids. Mass spectrometric measurement on the obtained solids showed a peak at M/Z=318.

Finally, a mixture of 2.8 g of the diquinone compound thus synthesized, 2.9 g of malononitrile, and 120 ml of pyridine was heated under stirring at 50° C. for 8 h. After allowing the mixture to cool, the solids were collected by filtration, washed with water, methanol, and then toluene, vacuum-dried, and purified by sublimation at 300° C., to obtain 2.2 g of purple crystals. Through IR measurement of the obtained compound, it was found that the absorption at 1720 cm$^{-1}$ attributable to carbonyl group disappeared and the absorption attributable to cyano group appeared at 2220 cm$^{-1}$. Mass spectrometric measurement showed a peak at M/Z=414.

The obtained compound was measured for the reduction potential by cyclic voltammetry in the same manner as in Example 1. The reduction potential of the compound (A-3) on the basis of the first oxidation potential of the standard ferrocene (Fc) was −0.87 V (vs Fc$^+$/Fc).

Example 8

Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min.

The cleaned glass substrate was mounted to a substrate holder of a vacuum vapor deposition apparatus. The compound (A-1) synthesized in Example 1 and the compound (C-1) shown below in a molar ratio of 2:98 were deposited into a film of 60 nm thick so as to cover the transparent electrode. The film of the mixture worked as a hole injecting layer.

Successively, the compound (HTM-1) shown below was made into a film of 20 nm thick on the mixed film. The obtained film worked as a hole transporting layer.

The compound (EM1) and the amine compound (D1) having a styryl group (light emitting molecule) were deposited into a film of 40 nm thick in a weight ratio of EM1:D1=40:2. The obtained film worked as a light emitting layer.

A 10-nm thick Alq film was further formed on the film thus formed, which worked as an electron injecting layer. Thereafter, Li serving as a reductive dopant (Li source: manufactured by SAES Getters Co., Ltd.) and Alq were co-deposited, to form an Alq:Li film (10 nm thick) as an electron injecting layer (cathode). Metal Al is vapor-deposited on the Alq:Li film to form a metal cathode, thereby obtaining an organic EL device.

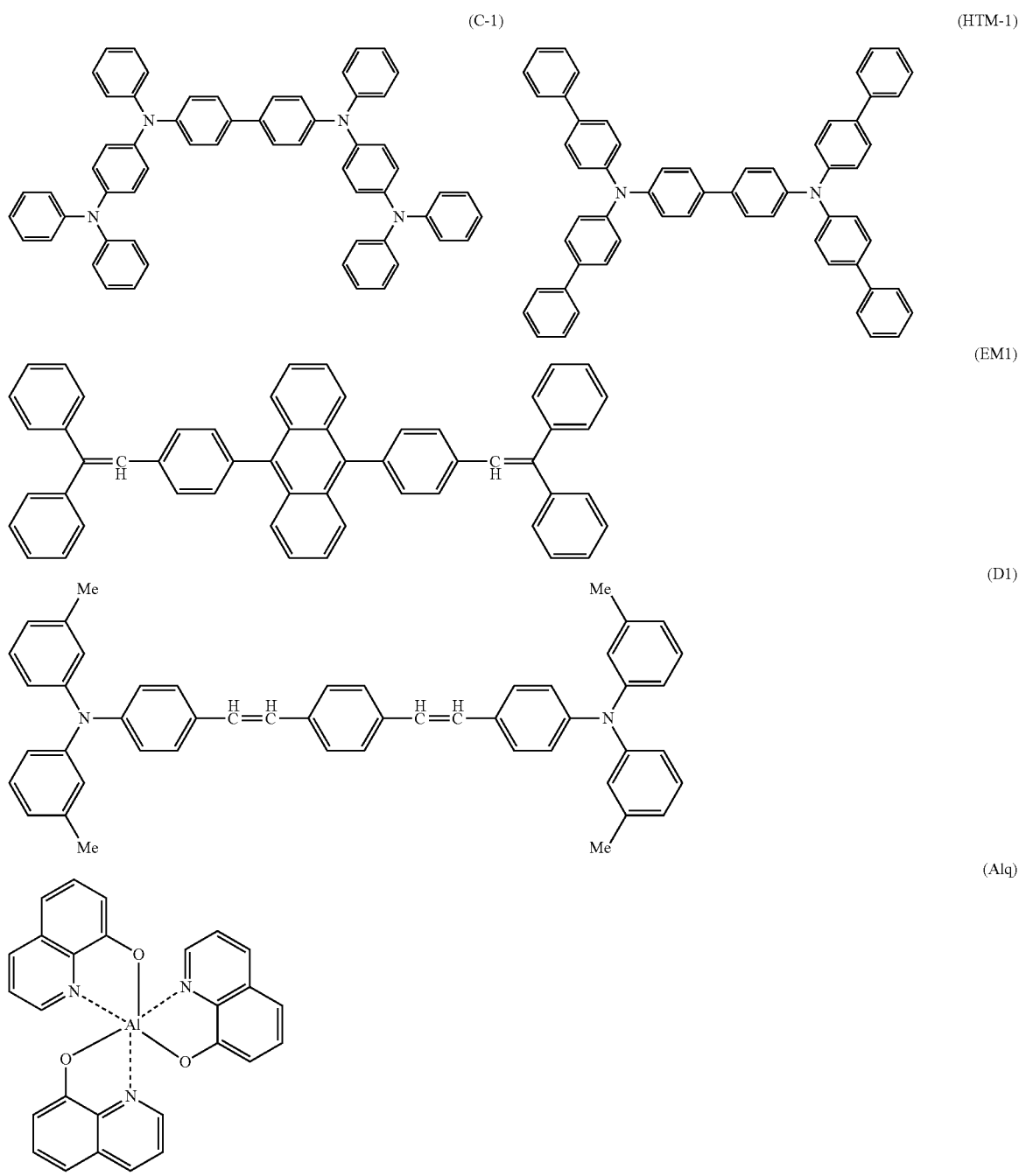

The organic EL device thus produced was measured for the driving voltage at a current density of 10 mA/cm² and the half lifetime of light emission when driven by constant DC current at an initial luminance of 1000 nit at room temperature. The results are shown in Table 1.

Example 9 to 13

An organic EL device was produced in the same manner as in Example 8 except for forming the hole injecting layer into a 10 nm thick film of each material shown in Table 1 and changing the thickness of the HTM-1 film (hole transporting layer) to 70 nm. The results of evaluation are shown in Table 1.

Example 14

An organic EL device was produced in the same manner as in Example 8 except for changing the compound (A-1) to the compound (A-23). The results of evaluation are shown in Table 1.

Comparative Example 1

An organic EL device was produced in the same manner as in Example 8 except for forming the hole injecting layer from the compound (C-1) alone. The results of evaluation are shown in Table 1.

TABLE 1

|  | Material of hole injecting layer | Driving voltage (V) | Half lifetime (h) |
|---|---|---|---|
| Examples | | | |
| 8 | A-1 C-1 | 6.1 | 6,900 |
| 9 | A-1 | 6.1 | 6,800 |
| 10 | A-5 | 6.5 | 6,000 |
| 11 | A-49 | 5.9 | 7,000 |
| 12 | A-55 | 5.7 | 7,100 |
| 13 | A-64 | 5.8 | 7,000 |
| 14 | A-23 C-1 | 6.0 | 6,700 |
| Comparative Example | | | |
| 1 | C-1 | 6.6 | 5,000 |

Industrial Applicability

The indenofluorenedione derivative of the invention is useful as the material for organic EL devices.

The material for organic EL devices of the invention is useful as a material forming the organic EL device, particularly, as a material for a hole transporting layer and a hole injecting layer.

The organic EL device of the invention is suitable as a light source, such as a backlight of flat emitter and display, a display of cellular phone, PDA, automotive navigation system, and automotive instrument panel, and a lighting equipment.

What is claimed is:

1. An indenofluorenedione derivative represented by formula (I):

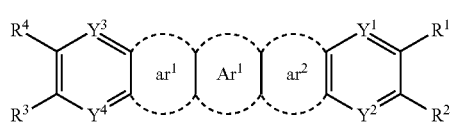

wherein
Ar$^1$ is a benzene ring or a naphthalene ring, each of which may be substituted by a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxyl group, a substituted or unsubstituted fluoroalkoxyl group, a substituted or unsubstituted aryloxy group, a substituted or unsubstituted aralkyloxy group, a substituted or unsubstituted amino group, or cyano group, ar$^1$ and ar$^2$ may be the same or different and each independently represent a structure represented by formula (i) or (ii):

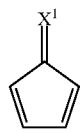

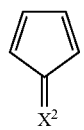

wherein X$^1$ and X$^2$ may be the same or different and selected from the following divalent groups represented by formulae (a) to (g):

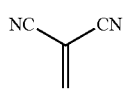

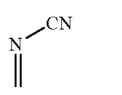

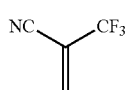

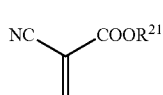

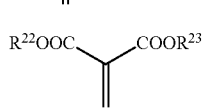

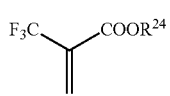

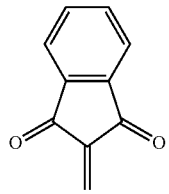

wherein R$^{21}$ to R$^{24}$ may be the same or different and each independently represent a hydrogen atom, a substituted or unsubstituted fluoroalkyl group, a substituted or unsubstituted alkyl group, a substituted or unsubstituted cycloalkyl group, a substituted or unsubstituted aryl group, or a substituted or unsubstituted heterocyclic group, and R$^{22}$ and R$^{23}$ may bond to each other to form a ring, R$^1$ to R$^4$ may be the same or different and each independently represent a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxyl group, a substituted or unsubstituted fluoroalkoxyl group, a substituted or unsubstituted aryloxy group, a substituted or unsubstituted aralkyloxy group, a substituted or unsubstituted amino group, or cyano group, and $R^1$ and $R^2$, and $R^3$ and $R^4$ may bond to each other to form a saturated or unsaturated divalent group completing a ring, and $Y^1$ to $Y^4$ may be the same or different and each represent —N=, —CH=, or —C($R^5$)=, wherein $R^5$ is defined in the same manner as in $R^1$ to $R^4$, and adjacent groups of $R^1$ to $R^5$ may bond to each other to form a saturated or unsaturated divalent group completing a ring, wherein the indenofluorenedione derivative represented by formula (I) does not include a compound represented by formula (iii):

(iii)

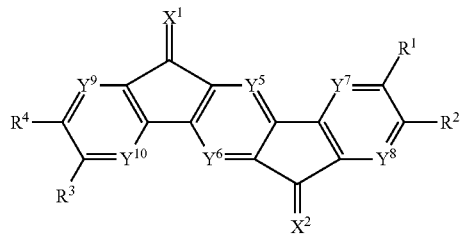

wherein $X^1$ and $X^2$ are defined in the same manner as in formula (I); $R^1$ to $R^4$ are defined in the same manner as in $R^1$ to $R^4$ of formula (I), and $Y^5$ to $Y^{10}$ are defined in the same manner as in $Y^1$ to $Y^4$ of formula (I).

2. The indenofluorenedione derivative according to claim 1, which is represented by any one of formulae (II) to (VII):

(II)

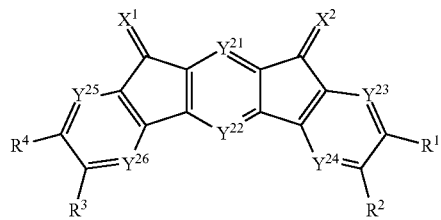

(III)

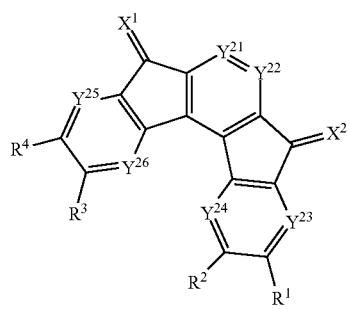

(IV)

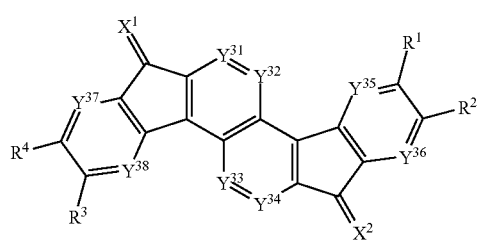

(V)

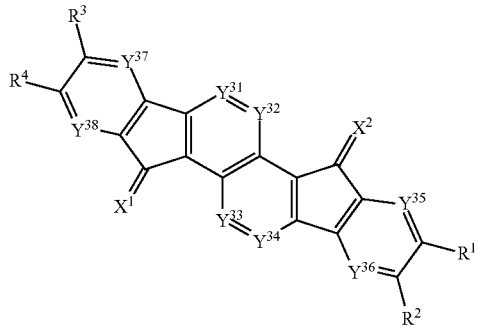

(VI)

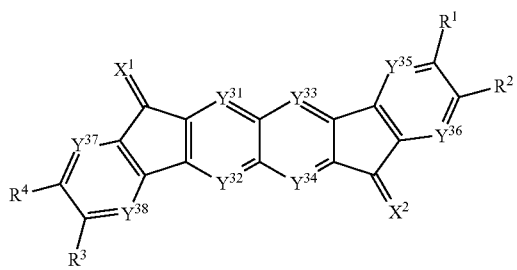

(VII)

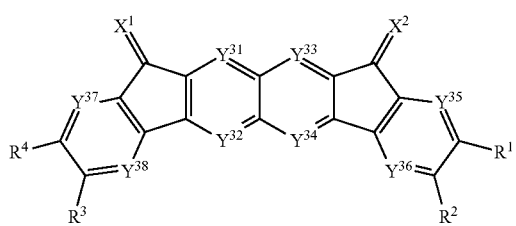

wherein $X^1$, $X^2$, and $R^1$ to $R^4$ are defined in the same manner as in formula (I) and $Y^{21}$ to $Y^{26}$ and $Y^{31}$ to $Y^{38}$ are defined in the same manner as in $Y^1$ to $Y^4$ of formula (I).

3. The indenofluorenedione derivative according to claim 1, wherein at least one of $Y^1$ to $Y^4$ of formula (I) is a nitrogen atom.

4. The indenofluorenedione derivative according to claim 1, wherein at least one of $R^1$ to $R^4$ of formula (I) is selected from the group consisting of a fluorine atom, a fluoroalkyl group, a fluoroalkoxyl group, a cyano group, an aryl group and a heterocyclic group, wherein each of the aryl group and the heterocyclic group has at least one substituent selected from the group consisting of fluorine, a fluoroalkyl group, a fluoroalkoxyl group, and a cyano group.

5. A material for organic electroluminescence devices comprising the indenofluorenedione derivative as defined in claim 1.

6. The material for organic electroluminescence devices according to claim 5, which has a reduction potential of −1.0 V vs. Fc$^+$/Fc, wherein Fc is ferrocene, when measured in an acetonitrile solution.

7. The material for organic electroluminescence devices according to claim 5, which is a hole injecting material.

8. An organic electroluminescence device comprising an anode, a cathode, and an organic thin layer between the anode and the cathode, wherein the organic thin layer comprises the material for organic electroluminescence devices as defined in claim 5.

9. The organic electroluminescence device according to claim 8, wherein the organic thin layer is a laminate comprising a hole injecting layer, a hole transporting layer, a light emitting layer, and an electron transporting layer in this order from a side of the anode, and the hole injecting layer comprises the material for organic electroluminescence devices.

10. The indenofluorenedione derivative according to claim 1, wherein $Ar^1$ is a benzene ring or a naphthalene ring;

$ar^1$ and $ar^2$ may be the same or different and each independently represent a structure represented by formula (i) or (ii):

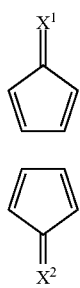

wherein $X^1$ and $X^2$ may be the same or different and selected from the following divalent groups represented by formulae (a) and (b):

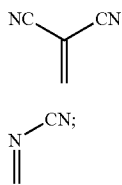

$R^1$ to $R^4$ may be the same or different and each independently represent a hydrogen atom, a substituted aryl group wherein the substituent is at least one selected from the group consisting of a halogen atom, a cyano group, a fluoroalkyl group and a fluoroalkoxyl group, a halogen atom, a substituted or unsubstituted fluoroalkyl group, a substituted or unsubstituted fluoroalkoxyl group, or a cyano group, and $Y^1$ to $Y^4$ may be the same or different and each represent —N= or —CH=.

11. The indenofluorenedione derivative according to claim 10, wherein $Ar^1$ is a benzene ring.

12. The indenofluorenedione derivative according to claim 10, wherein each of $X^1$ and $X^2$ is represented by formula (a).

13. The indenofluorenedione derivative according to claim 10, wherein $R^1$ to $R^4$ each independently represent a hydrogen atom, a fluorine atom, a fluoroalkyl group, a fluoroalkoxyl group, or a cyano group.

14. The indenofluorenedione derivative according to claim 10, wherein each of $Y^1$ to $Y^4$ represents —CH=.

15. The indenofluorenedione derivative according to claim 1, wherein the indenofluorenedione derivative is represented by formula (I-A):

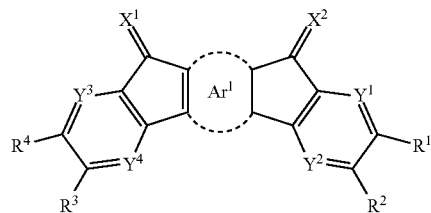

$Ar^1$ is a benzene ring or a naphthalene ring;

$X^1$ and $X^2$ may be the same or different and selected from the following divalent groups represented by formulae (a) and (b):

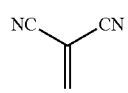

$R^1$ to $R^4$ may be the same or different and each independently represent a hydrogen atom, a substituted aryl group wherein the substituent is at least one selected from the group consisting of a halogen atom, a cyano group, a fluoroalkyl group and a fluoroalkoxyl group, a halogen atom, a substituted or unsubstituted fluoroalkyl group, a substituted or unsubstituted fluoroalkoxyl group, or a cyano group, and $Y^1$ to $Y^4$ may be the same or different and each represent —N= or —CH=.

16. The indenofluorenedione derivative according to claim 15, wherein $Ar^1$ is a benzene ring.

17. The indenofluorenedione derivative according to claim 15, wherein each of $X^1$ and $X^2$ is represented by formula (a).

18. The indenofluorenedione derivative according to claim 15, wherein $R^1$ to $R^4$ each independently represent a hydrogen atom, a fluorine atom, a fluoroalkyl group, a fluoroalkoxyl group, or a cyano group.

19. The indenofluorenedione derivative according to claim 15, wherein each of $Y^1$ to $Y^4$ represents —CH=.

20. The indenofluorenedione derivative according to claim 1, wherein the indenofluorenedione derivative is represented by formula

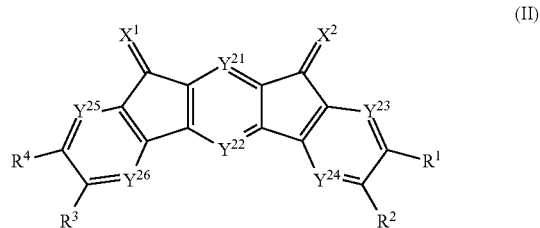

wherein $X^1$ and $X^2$ may be the same or different and selected from the following divalent groups represented by formulae (a) and (b):

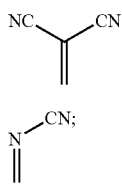

(a)

(b)

R¹ to R⁴ may be the same or different and each independently represent a hydrogen atom, a substituted aryl group wherein the substituent is at least one selected from the group consisting of a halogen atom, a cyano group, a fluoroalkyl group and a fluoroalkoxyl group, a halogen atom, a substituted or unsubstituted fluoroalkyl group, a substituted or unsubstituted fluoroalkoxyl group, or a cyano group, and $Y^{21}$ to $Y^{26}$ may be the same or different and each represent —N= or —CH=.

21. The indenofluorenedione derivative according to claim 20, wherein $Ar^1$ is a benzene ring.

22. The indenofluorenedione derivative according to claim 20, wherein each of $X^1$ and $X^2$ is represented by formula (a).

23. The indenofluorenedione derivative according to claim 20, wherein $R^1$ to $R^4$ each independently represent a hydrogen atom, a fluorine atom, a fluoroalkyl group, a fluoroalkoxyl group, or a cyano group.

24. The indenofluorenedione derivative according to claim 20, wherein each of $Y^{21}$ to $Y^{26}$ represents —CH=.

25. The organic electroluminescence device according to claim 8,
wherein the organic thin layer comprises a hole injecting layer and the hole injecting layer comprises the material for organic electroluminescence devices.

26. The organic electroluminescence device according to claim 8,
wherein the organic thin layer comprises a hole injecting layer and a hole transporting layer and the hole injecting layer comprises the material for organic electroluminescence devices.

27. The organic electroluminescence device according to claim 26,
wherein the hole transporting layer comprises at least one material selected from the group consisting of a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, a polysilane-based copolymer, an aniline-based copolymer, and an electrically conductive high-molecular oligomer.

* * * * *